(12) United States Patent
Baciu et al.

(10) Patent No.: US 9,701,743 B2
(45) Date of Patent: Jul. 11, 2017

(54) COMPLEMENT COMPONENT C5 ANTIBODIES

(71) Applicant: Allergan, Inc., Irvine, CA (US)

(72) Inventors: Peter C. Baciu, Laguna Niguel, CA (US); Yanbin Liang, Irvine, CA (US); Jason Guu, Yorba Linda, CA (US); Matthew Bernett, Monrovia, CA (US); Umesh Muchhal, Monrovia, CA (US); John Desjarlais, Monrovia, CA (US)

(73) Assignee: Allergan, Inc., Irvine, CA (US)

( * ) Notice: Subject to any disclaimer, the term of this patent is extended or adjusted under 35 U.S.C. 154(b) by 85 days.

(21) Appl. No.: 14/626,514

(22) Filed: Feb. 19, 2015

(65) Prior Publication Data
US 2015/0239966 A1   Aug. 27, 2015

Related U.S. Application Data

(60) Provisional application No. 61/944,943, filed on Feb. 26, 2014.

(51) Int. Cl.
| | | |
|---|---|---|
| *A61K 39/395* | (2006.01) | |
| *C07K 16/18* | (2006.01) | |
| *A61K 39/00* | (2006.01) | |

(52) U.S. Cl.
CPC .............. *C07K 16/18* (2013.01); *A61K 39/00* (2013.01); *A61K 39/0005* (2013.01); *A61K 39/3955* (2013.01); *C07K 2317/24* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 3,691,016 A | 9/1972 | Ravindra Patel | |
| 3,773,919 A | 11/1973 | Boswell et al. | |
| 3,969,287 A | 7/1976 | Jaworek et al. | |
| 4,179,337 A | 12/1979 | Davis et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,301,144 A | 11/1981 | Iwashita et al. | |
| 4,330,440 A | 5/1982 | Ayers et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly | |
| 4,965,195 A | 10/1990 | Namen et al. | |
| 4,968,607 A | 11/1990 | Dower et al. | |
| 5,292,658 A | 3/1994 | Cormier et al. | |
| 5,418,155 A | 5/1995 | Cormier et al. | |
| 5,683,888 A | 11/1997 | Campbell | |
| 5,741,668 A | 4/1998 | Ward et al. | |
| 5,777,079 A | 7/1998 | Tsien et al. | |
| 5,804,387 A | 9/1998 | Cormack et al. | |
| 5,874,304 A | 2/1999 | Zolotukhin et al. | |
| 5,876,995 A | 3/1999 | Bryan | |
| 5,925,558 A | 7/1999 | Tsien et al. | |
| 6,172,197 B1 | 1/2001 | McCafferty | |
| 6,248,516 B1 | 6/2001 | Winter et al. | |
| 6,291,158 B1 | 9/2001 | Winter et al. | |
| 6,582,915 B1 | 6/2003 | Griffiths et al. | |
| 6,593,081 B1 | 7/2003 | Griffiths et al. | |
| 6,696,245 B2 | 2/2004 | Winter et al. | |
| 7,657,380 B2 | 2/2010 | Lazar et al. | |
| 7,930,107 B2 | 4/2011 | Lazar et al. | |
| 2004/0110941 A2 | 6/2004 | Winter et al. | |
| 2006/0008883 A1 | 1/2006 | Lazar et al. | |
| 2008/0167449 A1 | 7/2008 | Lazar et al. | |
| 2011/0236969 A1 | 9/2011 | Lazar et al. | |
| 2012/0225056 A1* | 9/2012 | Rother .................. | C07K 16/18 424/133.1 |

FOREIGN PATENT DOCUMENTS

| | | |
|---|---|---|
| EP | 0088046 | 2/1983 |
| EP | 0036676 | 7/1984 |
| EP | 0133988 | 8/1984 |
| EP | 0143949 | 10/1984 |
| EP | 0281482 | 9/1988 |
| EP | 0367566 | 10/1989 |
| EP | 0460846 | 2/2002 |
| EP | 0368684 | 9/2004 |
| WO | 87-05330 | 9/1987 |
| WO | 94-13804 | 6/1994 |
| WO | 95-07463 | 3/1995 |

(Continued)

OTHER PUBLICATIONS

Rudikoff et al. Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Giclas, P.C. et al, Preparation and Characterization of Monoclonal Antibodies Against the Fifth Component of Rabbit Complement (C5), Journal of Immunological Methods, 1987, 201-209, 105.
Klos, A. et al, Detection of Native Human Complement Components C3 and C5 and Their Primary Activation Peptides C3a and C5a (Anaphylatoxic Peptides) by ELISAs with Monoclonal Antibodies, Journal of Immunological Methods, 1988, 241-252, 111.

(Continued)

*Primary Examiner* — Phillip Gambel
(74) *Attorney, Agent, or Firm* — Brigitte C. Phan; Ted A. Chan

(57) ABSTRACT

The present disclosure relates to antibodies and polynucleotides encoding the same, that may be used to prevent, control, or reduce the activity of the complement pathway. In addition, the disclosure is directed to compositions and methods for diagnosing and treating diseases mediated by or involving complement C5. Specifically, the disclosure is related to C5 antibodies.

14 Claims, 16 Drawing Sheets

(56) References Cited

FOREIGN PATENT DOCUMENTS

| WO | 96-39154 | 12/1996 |
|----|----------|---------|
| WO | 97-03211 | 1/1997 |
| WO | 98-26277 | 6/1998 |
| WO | 99-49019 | 9/1999 |
| WO | 03-002609 | 1/2003 |
| WO | 2004-003019 | 1/2004 |
| WO | 2004-058821 | 7/2004 |
| WO | 2010-054403 | 5/2010 |

OTHER PUBLICATIONS

Mollnes, T.E. et al, Identification of a Human C5 β-Chain Epitope Exposed in the Native Complement Component But Concealed in the SC5b-9 Complex, Sand. J. Immunol., 1988, 307-312, 28.

\* cited by examiner

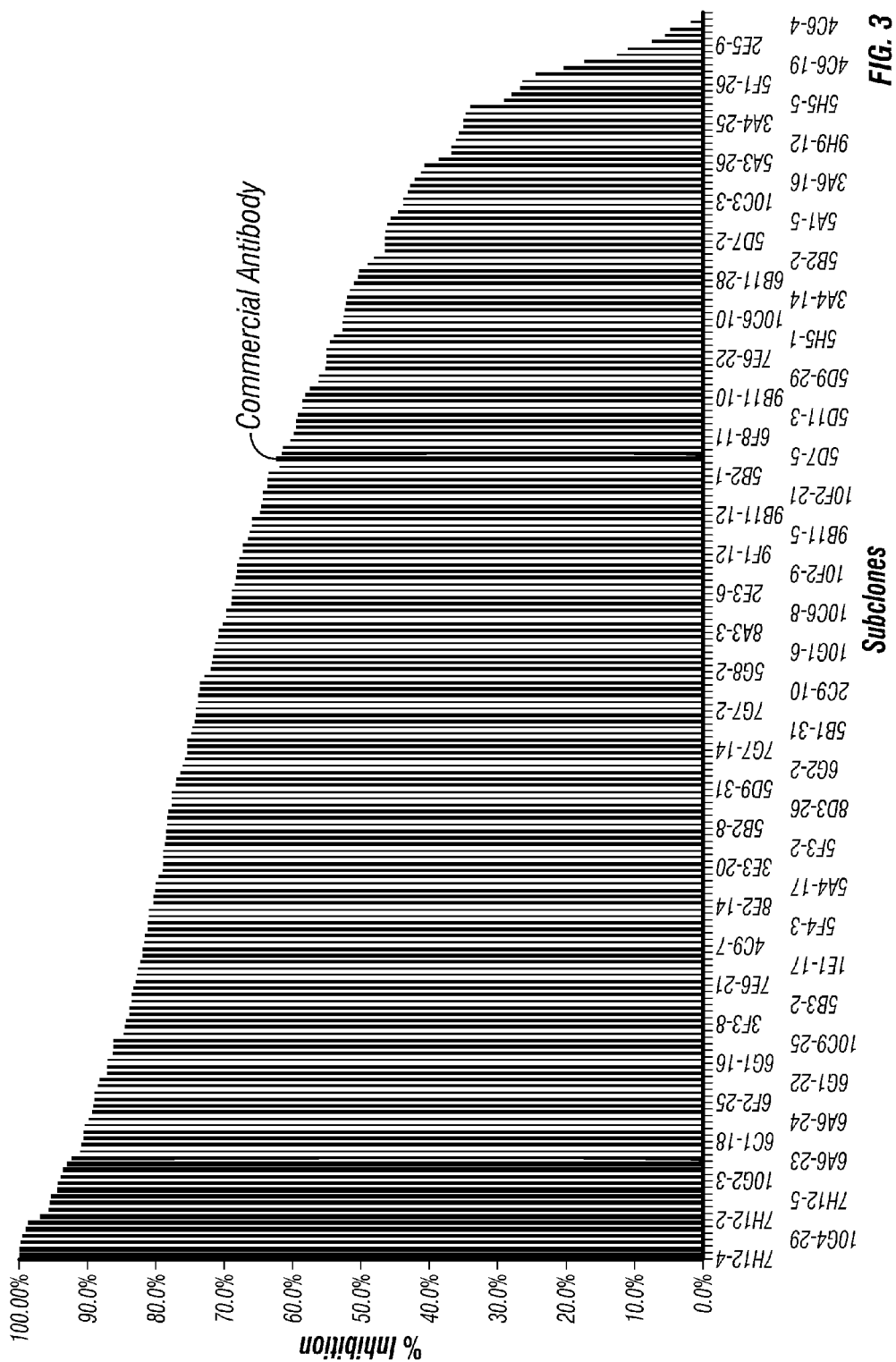

| Clone ID | Kd | K[on] | K[off] | r Squared |
|---|---|---|---|---|
| 10C9-19 | 1.444E-12 | 3.84E+05 | 5.55E-07 | 0.993054 |
| 1B6-10H11 | 1.626E-10 | 1.78E+05 | 2.89E-05 | 0.921366 |
| 2A12-13H10 | 5.591E-11 | 1.56E+05 | 8.69E-06 | 0.984873 |
| 4G12-1D9 | 9.286E-11 | 1.85E+05 | 1.72E-05 | 0.967668 |
| 6C12-8C10 | 5.427E-11 | 1.12E+05 | 6.05E-06 | 0.989999 |
| 6C12-9H9 | 6.505E-11 | 1.51E+05 | 9.82E-06 | 0.973618 |
| 6H7-19D11 | 4.021E-11 | 1.70E+05 | 6.85E-06 | 0.96237 |
| 7B1-10H9 | 2.352E-10 | 4.05E+05 | 9.53E-05 | 0.929208 |
| 7B12-5H5 | 2.626E-11 | 9.45E+04 | 2.48E-06 | 0.975405 |
| 7C1-6C7 | 1.463E-11 | 1.38E+05 | 2.02E-06 | 0.958707 |
| 8A8-11F9 | 1.052E-09 | 3.47E+04 | 3.65E-05 | 0.976231 |
| 8H10-2D9 | 2.554E-10 | 2.88E+05 | 7.36E-05 | 0.97153 |
| 10B11-30H9 | 6.891E-11 | 3.05E+05 | 2.10E-05 | 0.975237 |

| Clone | Displacement @ 300s. |
|---|---|
| 10G4 | 0.72 |
| 7B1 | -0.02 |
| 8C7 | 0.08 |
| 10C9-19r | 0.01 |
| A239 | 0.86 |

COMPLEMENT COMPONENT C5 ANTIBODIES

CROSS-REFERENCE

This application claims priority under 35 U.S.C. §119(e) from U.S. Provisional Application Ser. No. 61/768,374, filed Feb. 20, 2014, and U.S. Provisional Application Ser. No. 61/944,943, filed Feb. 26, 2014, both of which is hereby incorporated by reference in their entirety.

TECHNICAL FIELD OF THE INVENTION

The present disclosure relates to antibodies and compositions thereof, polynucleotides encoding the same, expression vectors and host cells for production of the antibodies, and compositions and methods for diagnosing and treating diseases mediated by complement.

BACKGROUND OF THE INVENTION

The complement system is composed of nearly 50 individual proteins that functions as a part of the innate immune system providing the initial phase of host defense, opsonization of foreign material, and tissue homeostasis. (Ricklin D., 2010, Complement: a Key system for immune surveillance and homeostasis. *Nature: Immunology,* 785-795) The complement system is found in all multicellular organism and phylogenetically predates the formation of the adaptive immune system (Zarkadis I. K., 2001 Phylogenetic aspects of the complement system. *Development and Comparative Immunology,* 745-762.). Activation of the complement system occurs along three primary pathways: classical, lectin and alternative pathways. FIG. 1 shows a schematic representation of the three primary complement pathways. See also, Donoso, et al., "The Role of Inflammation in the Pathogenesis of Age-related Macular Degeneration", *Survey of Ophthalmology,* Vol. 51, No. 2, March-April 2006.

During the activation process sequential protein-protein interactions and proteolytic activity leads to the generation of the C3 and C5 convertases. These convertases are responsible for producing complement activation split products that represent the effector molecules of the complement cascade important for opsonization, generation of anaphylatoxins, and the formation of the membrane attack complex (MAC). The latter of these is essential for the lytic activity of the complement cascade (Ricklin D., 2010). Under normal conditions activation of the complement cascades provides defense against pathogenic bacterial, viruses as well as clearance of diseased and injured tissue. Normally, the formation of MAC does not affect surrounding tissue due to the presence of cell surface and soluble regulatory components which include CFH, CFH related proteins, C4BP, CD46, CD55, CD59 and complement factor I (CFI). However, when excess activation occurs or when there is a failure in complement regulatory components, both acute and chronic disease states are induced. Examples in which uncontrolled complement activation is recognized as causative to human pathologies include: Glomerulonephritis, Systemic Lupus Erythematosus, Paroxysmal Nocturnal Hemoglobinuria, Alzheimer's, Hereditary Angioedema, Myasthenia Gravis and Age-related Macular Degeneration (AMD) (Ricklin & Lambris, 2013, Complement in Immune and inflammatory Disorders:Pthaological Mechanisms. *Journal of Immunology,* 3831-3838).

C5 is a 190 kDa protein comprising two polypeptide chains (α, 115 kDa and β, 75 kDa) that are linked together by disulfide bonds. C5 convertase cleaves at an arginine residue 75 amino acids downstream from the C5 α-chain N terminus generating the 7.4 Kd C5a and 180 Kd C5b complement split products. The C5b component serves as the initiation component for the assembly of the membrane attack complex (MAC) through the sequential addition of C6, C7, C8 and C9. The C6-C8 subunits assemble in a 1:1 relationship to C5b while multiple C9 subunits are incorporate into the complex generating a non-specific pore in both prokaryotic and eukaryotic plasma membranes FIG. 2. See also, Bubeck D., 2014, "The making of a macromolecular machine: assembly of the membrane attack complex" *Biochemistry,* 53(12):1908-15. The formation of MAC on the cell surface has several consequences for the cells. At high levels the unregulated influx and efflux of solutes leads to cellular swelling and eventual cell lysis. This causes the uncontrolled release of cellular material promoting a pro-inflammatory environment and cellular loss. Formation of MAC at sublytic concentrations on the cell surface can contribute to release of pro-inflammatory and pro-agniogenic cytokines and growth factors, elevation in cellular stress and eventual necrotic cell death.

Age-related Macular Degeneration (AMD) is the leading cause of blindness in the elderly developed countries. In the US population alone the prevalence of advanced forms of AMD associated with vision loss occurs in nearly 2 million individuals. Another 7 million individuals with intermediate AMD are at a high risk for development of advanced forms of AMD. Inclusion of the European population nearly doubles the number of impacted individuals. AMD is characterized by a progressive loss of vision attributable to a para-inflammatory process causing the progressive degeneration of the neuroretina, and support tissues which include the retinal pigmented epithelium (RPE) and choriocapillaris. The majority of clinically significant vision loss occurs when the neurodegenerative changes impact the center of the retina within a highly specialized region of the eye responsible for fine visual acuity, the macula. The disease has a tremendous impact on the physical and mental health of the individual due to vision loss and increased dependence on family members to perform everyday tasks.

The deregulation of the complement system is highly correlated with the development of AMD. First, genetic mutations in over 20 genes have been correlated with a person's risk of developing AMD, accounting for an estimated 70% of total risk. (Fritsche et al., "Age related Macular Degeneration: Genetics and Biology Coming Together", *Annu Rev Genomics Hum Genet.* 2014; 15:151-71). Within these 20 genes, five are complement genes, which alone account for 57% of total risk in the development of the advanced forms of AMD. In addition, AMD-related inflammation and associated deregulation of complement activity, as indicated by elevation of complement activation products in systemic circulation and in AMD tissues by histopathological analysis, occurs in the absence of known genetic polymorphisms in complement proteins. New discoveries, have highlighted the potential pathological impact of complement by the identification of and presence of the membrane attack complex in diseased tissue and in occurrence of advanced forms of AMD (Whitmore S, et al. 2014, "Complement activation and choriocapillaris loss in early AMD: Implications for pathophysiology and therapy." *Progress in Retinal and Eye Research,* Dec. 5, 2014 EPub ahead of print; Nishigauchi K M, et al. 2012 "C9-R95X polymorphism in patients with neovascular age-related macular degeneration", January 131; 53(1) 508-12). These results suggest the viability of blocking the final complement pathway component as a therapeutic target for treating AMD. To date most therapeutics targeting formation of MAC do so by blocking the formation of C5b the key building block required to initiate MAC formation. However, in doing so they also block formation of C5a resulting in loss of C5a functional activity that has been associated with tissues homeostasis (removal of opsinized particles), neural survival and promotion of an anti-angiogenic response. In man, this process of selectively blocking MAC formation is usually carried out by the cell surface protein CD59 which blocks MAC assembly and by the soluble factors vitronectin and clusterin. In order to mimic the natural mechanism and preserve favorable upstream activities of complement activation the current application reveals the development of a novel therapeutic monoclonal antibody that binds C5 but uniquely allows processing of the C5 molecule to C5a and C5b but inhibits formation of MAC, FIG. 2, thus preventing formation of the key pathogenic component associated with AMD. Through blocking MAC formation, while preserving key supportive ocular tissues i.e., choroicapilars and RPE, function and survival of the neural retina, which is vital to maintaining vision will be retained.

SUMMARY OF THE INVENTION

The invention encompasses methods and compositions of a pharmaceutical formulation comprising an anti-complement C5 antibody or anti-C5 antibody. In one aspect, the anti-C5 antibody does not bind to C5a and inhibits complement dependent hemolysis. In another aspect, the anti-C5 antibody binds to C5b and inhibits the formation of membrane attack complex (MAC) in a patient. In one embodiment, the anti-C5 antibody blocks C5 binding to human complement component 6. In another embodiment, the anti-C5 antibody blocks C5 binding to human complement component 7. In another aspect, the anti-C5 antibody is characterized by the feature that it no longer binds or has reduced binding to C5 (or a subunit thereof) once it is incorporated into the membrane attack complex.

In another aspect, the anti-complement C5 antibody or anti-C5 antibody binds to C5 with a Kd of less than about 10 pM. In another aspect, the anti-C5 antibody is a monoclonal antibody. In another embodiment, the anti-C5 antibody is selected from the group consisting of a monoclonal antibody, a polyclonal antibody, a recombinant antibody, a humanized antibody, a chimeric antibody, a multispecific antibody and an antibody fragment. In one embodiment, the anti-C5 antibody is an antibody fragment and that antibody fragment is a Fab fragment, a Fab' fragment, a F(ab')$_2$ fragment, a Fv fragment, a diabody, or a single chain antibody molecule. In another embodiment, the anti-C5 antibody is an IgG1, IgG2, IgG3, or IgG4. In another embodiment, the anti-C5 antibody is an IgG1.

In another aspect, the anti-C5 antibody is coupled to a labelling group. In another embodiment, the anti-C5 antibody is coupled to a labelling group and that labelling group is an optical label, radioisotope, radionuclide, an enzymatic group, and a biotinyl group.

In another aspect, the invention comprises a process for preparing an isolated antibody that binds to complement C5 comprising isolating said antibody from a host cell that secretes the antibody.

In another aspect, the invention is an anti-complement C5 antibody comprising an amino acid sequence selected from the group consisting of SEQ ID NOs: 13, 18, 23, 28, 33, and 38. In another aspect, the anti-C5 antibody comprises an amino acid sequence selected from the group consisting of SEQ ID NOs: 14, 19, 24, 29, 34 and 39. In another aspect, the anti-C5 antibody comprises an amino acid sequence selected from the group consisting of GTS, SGS, RTS, YTS, and WAS. In another aspect, the anti-C5 antibody comprises an amino acid sequence selected from the group consisting of SEQ ID NOs: 15, 20, 25, 30, 35 and 40. In another aspect, the anti-C5 antibody comprises an amino acid sequence selected from the group consisting of SEQ ID NOs: 16, 21, 26, 31, 36, and 41. In another aspect, the anti-C5 antibody comprises an amino acid sequence selected from the group consisting of SEQ ID NOs: 17, 22, 27, 32, 37 and 42. In another aspect, the invention is an antibody comprising a first and second amino acid sequence, the first amino acid sequence comprising a CDR1 selected from the group consisting of SEQ ID NOs: 13, 18, 23, 28, 33, and 38; a CDR2 selected from the group consisting of amino acid sequence GTS, SGS, YTS, and WAS; a CDR3 selected from the group consisting of SEQ ID NOs: 14, 19, 24, 29, 34 and 39; and a second amino acid sequence comprising a CDR1 selected from the group consisting of SEQ ID NOs: 15, 20, 25, 30, 35 and 40; a CDR2 selected from the group consisting of SEQ ID NOs: 16, 21, 26, 31, 36 and 41; and a CDR3 selected from the group consisting of SEQ ID NOs: 17, 22, 27, 32, 37 and 42. In other embodiment, the invention is an antibody comprising the amino acid sequence of SEQ ID NO: 10 and SEQ ID NO: 2.

In another aspect, the invention comprises a nucleic acid molecule encoding an isolated antibody that binds to complement C5. In one embodiment, the nucleic acid molecule encoding the antibody that binds to complement C5 is operably linked to a control sequence.

In another aspect, the invention comprises an anti-complement C5 antibody and a pharmaceutically acceptable carrier. In one embodiment, the anti-complement C5 antibody further comprises an additional active agent. In another embodiment, the anti-complement C5 antibody and additional active agent also include a pharmaceutically acceptable carrier.

In another aspect, the invention comprises a method for treating or preventing an indication in a patient in need of treatment or prevention, the method comprising administering to the patient, an effective amount of at least one anti-complement C5 antibody. In one embodiment, the indication is age-related macular degeneration (AMD). In another embodiment, the disease or disorder in a patient in need of treatment or prevention is an ocular condition.

BRIEF DESCRIPTION OF THE DRAWINGS

FIG. 3 shows percent inhibition of MAC by anti-C5 antibody sub-clones.

DETAILED DESCRIPTION OF THE INVENTION

Figure 1:
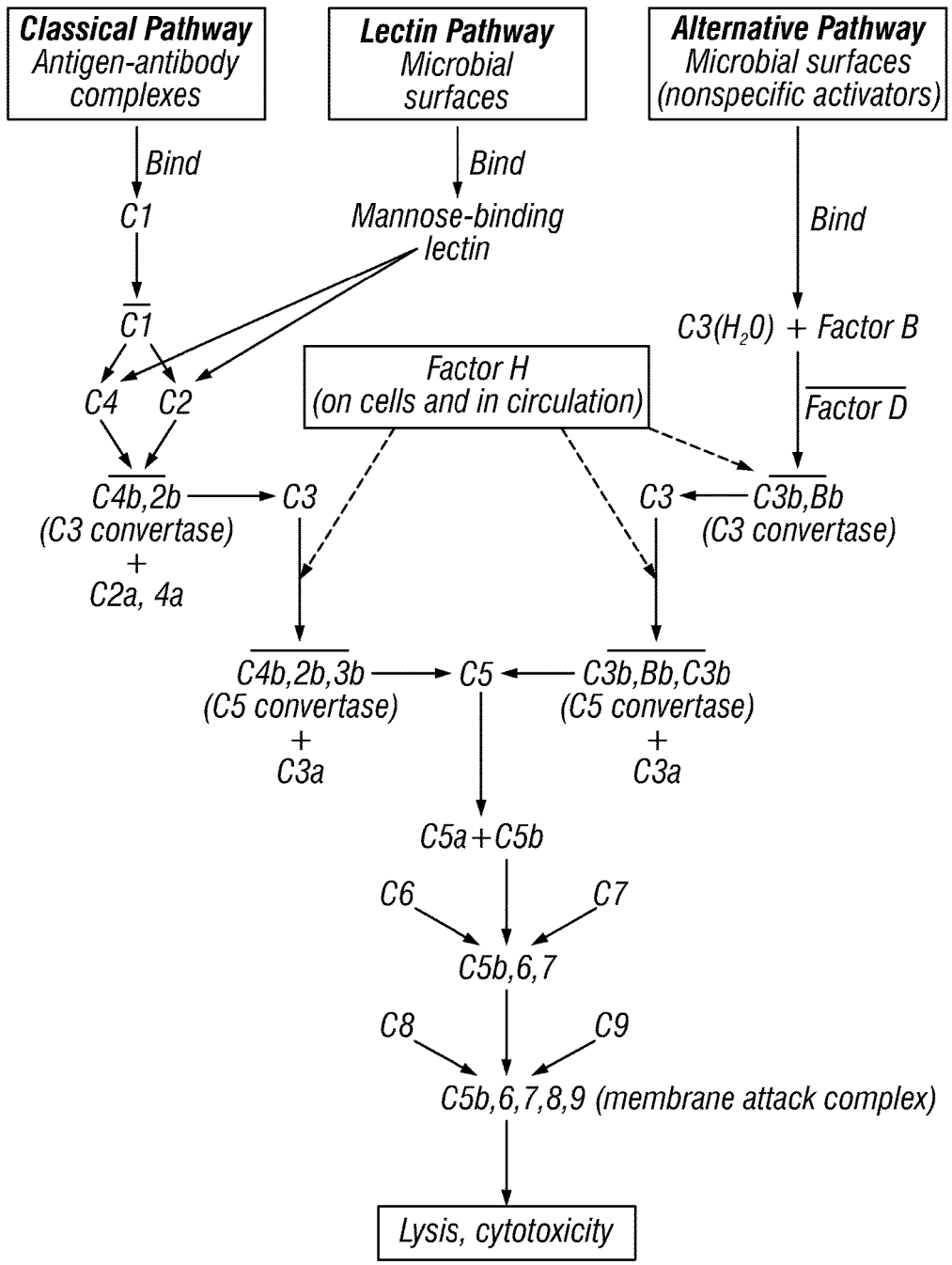
FIG. 1 shows a schematic of the Complement Pathway.

The section headings used herein are for organizational purposes only and are not to be construed as limiting the subject matter described.

Standard techniques can be used for recombinant DNA, oligonucleotide synthesis, tissue culture and transformation, protein purification etc. Enzymatic reactions and purification techniques can be performed according to the manufacturer's specifications or as commonly accomplished in the art or as described herein. The following procedures and techniques can be generally performed according to conventional methods well known in the art and as described in various general and more specific references that are cited and discussed throughout the specification. See, e.g., Sambrook et al., 2001, *Molecular Cloning: A Laboratory Manual*, 3$^{rd}$ ed., Cold Spring Harbor Laboratory Press, Cold Spring Harbor, N.Y., entirely incorporated by reference. Unless specific definitions are provided, the nomenclature used in connection with, and the laboratory procedures and techniques of, molecular biology, biological chemistry, physical and bio-physical chemistry, analytical chemistry, organic chemistry, and medicinal and pharmaceutical chemistry described herein are those well known and commonly used in the art. Standard techniques can be used for chemical synthesis, chemical analyses, pharmaceutical preparation, formulation, and delivery and treatment of patients.

The following definitions are used herein:

"AMD" refers to all forms of age related macular degeneration inclusive of but not limited to disease onset, (i.e. early and late), Disease stage (i.e early, intermediate or advance), Disease type (geographic atrophy or neovascular maculopathy), Disease distribution (ie. Unilateral, Bilateral, Central or Peripheryl), or presence/absence of drusen deposits, presence/absence of reticular pseudodrusen, retinal pigment epithelium abnormalities, photoreceptor abnormalities, atrophic age-related macular degeneration, geographic atrophy (GA) and neovascular maculopathy.

"Protein," as used herein, is meant to refer to at least two covalently attached amino acids, and is used interchangeably with polypeptides, oligopeptides, and peptides. The two or more covalently attached amino acids are attached by a peptide bond.

"C5" refers to human complement Component 5. As used herein, Factor C5, Component Factor 5 are synonymous with C5.

"C5a" refers the smaller fragment of C5 having approximately 77-74 amino acids and being about 7 kDa, that is produced when C5 is cleaved by C5 convertase when activated in the complement cascade. "C5b," refers to the larger fragment of C5 that is produced when cleaved by C5 convertase when activated in the complement cascade. C5b consists of an alpha chain (about 104 kDa) and a beta chain (about 75 kDa) linked by a single disulfide residue.

The terms "antibody" and "immunoglobulin" are used interchangeably in the broadest sense to refer to a protein, comprising one or more polypeptide chains that interact with a specific antigen, through binding of a plurality of CDRs on the antibody and an epitope of the antigen. An antibody can be a monoclonal (for e.g., full length or intact monoclonal antibodies), polyclonal, multivalent, and/or multispecific (e.g., bispecific antibodies so long as they exhibit the desired biological activity). Antibodies can also be or include antibody fragments (as described herein).

"Epitope" is used to refer to a sequence, structure, or moiety that is recognized and bound by an antibody. An epitope can be referred to as an "antigenic site."

"Antibody fragments" comprise only a portion of an intact antibody, wherein the portion retains at least one, most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcR binding, antibody half-life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

"Monoclonal" as used herein refers to an antibody obtained from a population of cells, wherein the population of cells is clonally-derived from a single parent cell. Monoclonal antibodies are homogeneous antibodies, i.e., the individual antibodies comprising the population are identical in that they are derived from the same genes and have the same amino acid sequence and protein structure except for possible naturally-occurring mutations that can be present in minor amounts and post-translational modifications that may, in some cases, be different. Monoclonal antibodies can, in some embodiments, be highly specific. In some embodiments, a monoclonal antibody can be directed against a single antigenic site. Furthermore, in contrast to other antibody preparations which typically include different antibodies directed against different determinants (epitopes), each monoclonal antibody is directed against the same epitope on the antigen. Individual monoclonal antibodies can be produced by any particular method. For example, the monoclonal antibodies to be used in accordance with the present disclosure can be made by the hybridoma method first described by Kohler et al. (1975) Nature 256:495, or can be made by recombinant DNA methods (see, e.g., U.S. Pat. No. 4,816,567), or from phage antibody libraries using the techniques described in Clackson et al. (1991) Nature 352: 624-628 and Marks et al. (1991) J. Mol. Biol. 222:581-597.

"Polyclonal" is used to describe a heterogeneous population of antibodies derived from a heterogeneous population of parent, antibody-producing cells. In most cases the polyclonal antibodies have different affinity for differing epitopes and are produced from genes with differing sequences.

"Chimeric" antibodies are antibodies comprising amino acid sequences derived from two or more different species.

"Humanized" antibodies are chimeric antibodies derived from a non-human parent antibody. In many cases specific amino acid positions in a humanized antibody, have been changed to correspond to the identity of the amino acid at a corresponding position in a human antibody. In many cases, positions in a variable region of the parent (non-human) antibody are replaced with amino acids from a variable region of a human species. This creates a humanized mouse, rat, rabbit or nonhuman-primate antibody having the desired specificity, affinity, and capacity.

"Variant" refers to sequences that comprise at least one difference compared to a parent sequence. A variant polypeptide is a protein having at least about 75% amino acid sequence identity to a parent sequence. A variant protein can have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with a parent amino acid sequence. In some cases variant antibodies are antibodies having one or more difference(s) in amino acid sequence as compared to a parent antibody. Humanized and chimeric antibodies are variant antibodies. Variant antibodies, therefore, comprise less than 100% sequence identity with a parent antibody. Variant nucleotide sequences comprise less than about 100% sequence identity with a parent nucleotide sequence.

"Isolated" or "purified" refers to a molecule that has been separated and/or recovered from at least one component of its natural environment, wherein the component is a material that can interfere with the use, or activity, of the molecule. Components include peptides, sugars, nucleic acids, enzymes, hormones, and other proteinaceous or nonproteinaceous solutes.

"Complementarity Determining Regions" (CDRs) refers to one or more regions within an antibody wherein the residues of one or more CDR aid in antigen binding. In many cases, individual amino acids of the CDRs can be in close proximity to atoms of the target antigen. In some embodiments the CDR may be located in an immunoglobulin that may be comprised of three CDR regions. In some cases, as where there are more than one CDR sequence in a larger amino acid sequence, the CDRs may be separated by other sequences, and the CDRs numbered. In some cases, multiple CDRs are identified as CDR1, CDR2 and CDR3. Each CDR may comprise amino acid residues from a Complementarity Determining Region as defined by Kabat. Kabat et al., Sequences of Proteins of Immunological Interest, 5th Ed. Public Health Service, National Institutes of Health, Bethesda, Md. (1991)) Amino acid numbering of CDRs, as well as other sequences within an antibody, or antibody fragment is according to that of Kabat. In many cases, CDRs can be defined by their position in a variable region sequence (numbering as in Kabat), for example the light chain CDR 1 may comprise the amino acid sequence between position 24 and position 33; between position 50 and position 56 for LC CDR2; and between position 89 and position 97 for LC CDR 3; and the heavy chain CDRs may lie between position 26 and position 33 for CDR1; position 50 and position 66 for HC CDR 2; and between position 97 and position 103 for HC CDR 3. and/or hypervariable loops may lie between light chain residues 26-32 (LC CDR1), residues 50-52 (LC CDR2) and residues 91-96 (LC CDR3); and heavy chain residues 26-32 (HC CDR1), residues 53-55 (HC CDR2) and residues 97-101 (HC CDR3). In some instances, a Complementarity Determining Region can include amino acids from both a CDR region defined according to Kabat and a hypervariable loop. In some embodiments, as in where the antibody is a single chain immunoglobulin, there may be more than one CDR, more than two CDRs, more than three CDRs, more than four CDRs, or more than five CDRs. In some embodiments, an antibody may be comprised of six CDRs.

"Framework regions," FRs, are variable domain residues other than the CDR residues. In most embodiments a variable domain has between two and four FRs identified sequentially. For example a variable region comprising three CDRs, has four FRs: FR1, FR2, FR3 and FR4. Where the CDRs are defined according to Kabat, the light chain FR residues are positioned at about residues 1-23 (LCFR1), 34-49 (LCFR2), 57-88 (LCFR3), and 98-107 (LCFR4) and the heavy chain FR residues are positioned about at residues 1-25 (HCFR1), 34-49 (HCFR2), 67-96 (HCFR3), and 104-113 (HCFR4) in the heavy chain residues. If the CDRs comprise amino acid residues from hypervariable loops, the light chain FR residues are positioned about at residues 1-23 (LCFR1), 34-49 (LCFR2), 57-88 (LCFR3), and 98-107 (LCFR4) in the light chain and the heavy chain FR residues are positioned about at residues 1-25 (HCFR1), 34-49 (HCFR2), 67-96 (HCFR3), and 104-113 (HCFR4) in the heavy chain residues. In some instances, when the CDR comprises amino acids from both a CDR as defined by Kabat and those of a hypervariable loop, the FR residues will be adjusted accordingly. For example, when HC CDR1 includes amino acids H26-H35, the heavy chain FR1 residues are at positions 1-25 and the FR2 residues are at positions 36-49.

"Variable domain" refers to portions of a light chain and a heavy chain of traditional antibody molecule that includes amino acid sequences of Complementarity Determining Regions (CDRs), and Framework Regions (FRs). VH refers to the variable domain of the heavy chain. VL refers to the variable domain of the light chain.

"Fv" or "Fv fragment" refers to an antibody fragment which contains a complete antigen recognition and binding site, comprising the FR and CDR sequences. In many embodiments, the Fv consists of a dimer of one heavy and one light chain variable domain in tight association, which can be covalent in nature, for example in a single chain Fv molecule (scFv). The three CDRs of each variable domain interact to define an antigen binding site on the surface of the VH-VL polypeptide. Collectively, the six CDRs or a subset thereof confer antigen binding specificity to the antibody. However, even a single variable domain (or half of an Fv comprising only three CDRs specific for an antigen) has, in some cases, the ability to recognize and bind antigen, although usually at a lower affinity than the entire binding site.

"Fab" or "Fab fragment" contains a variable and constant domain (CL) of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Percent (%) amino acid sequence identity" is defined as the percentage of amino acid residues in a candidate sequence that are identical with the amino acid residues in a reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Percent (%) amino acid sequence homology" is defined as the percentage of amino acid residues in a candidate sequence that are homologous with the amino acid residues in a reference sequence, after aligning the sequences and introducing gaps, if necessary, to achieve the maximum percent sequence homology. This method takes into account conservative substitutions. Conservative substitutions are those substitutions that allow an amino acid to be substituted with a similar amino acid Amino acids can be similar in several characteristics, for example, size, shape, hydrophobicity, hydrophilicity, charge, isoelectric point, polarity, aromaticity, etc. Alignment for purposes of determining percent amino acid sequence homology can be achieved in various ways that are within the ordinary skill of those persons of skill in the art. In some cases, amino acid sequences can be aligned using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence homology is then calculated relative to the longer sequence, i.e. even if a shorter sequence shows 100% sequence identity with a portion of a longer sequence, the overall sequence identity will be less than 100%.

"Percent (%) nucleic acid sequence identity" is defined as the percentage of nucleotides in a candidate sequence that are identical with the nucleotides in a reference sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Activity" or "biological activity" of a molecule can depend upon the type of molecule and the availability of tests for assaying a given activity. For example, in the context of a C5 antibody, activity refers to its ability to partially or fully inhibit a biological activity of C5, for example, binding to other complement proteins, cleavage by protease as exemplified by C5 convertase or other known protease of the extrinsic activation pathway capable of cleaving C5 (Krisinger M. J. et al., Thrombin generates previously unidentified C5 products that support the terminal complement activation pathway. Blood, 2012 120(8) 1717-1725), or MAC formation. A preferred biological activity of the claimed C5 antibody is the ability to block processes associated with activation of the C5 molecule. Preferably the inhibitory activity will achieve a measurable improvement in the state, e.g. pathology, of a C5-associated disease or condition, such as, for example, a complement-associated eye condition. In some cases, the activity inhibited by the disclosed anti-C5 antibody is through blocking a C5 protease or C5 cleavage. In other cases the activity is the ability to bind other complement proteins in a complex preventing membrane insertion and cell lysis. In some embodiments, the activity of the disclosed anti-C5 antibody is measured by its ability to inhibit hemolysis, C5a generation, MAC formation or association of other complement proteins with C5. The activity can be determined through the use of in vitro or in vivo tests, including binding assays, MAC formation assay, generation of complement split products, induction of cytokine release, or through the use of a relevant animal model, or human clinical trials.

"Complement-associated eye condition" is used in the broadest sense and includes all eye conditions the pathology of which involves complement, activated by either the classical, lectin, alternative or extrinsic pathways. Complement-associated eye conditions include, without limitation, macular degenerative diseases, such as all stages of age-related macular degeneration (AMD), including dry and exudative (non-exudative and exudative) forms, choroidal neovascularization (CNV), uveitis, diabetic and other ischemia-related retinopathies including diabetic macular edema, Central Retinal Vein Occlusion (CRVO), Branched Retinal Vein Occlusion (BRVO), and other intraocular neovascular diseases, such as diabetic macular edema, pathological myopia, von Hippel-Lindau disease, histoplasmosis of the eye, corneal neovascularization, and retinal neovascularization. A preferred group of complement-associated eye conditions includes age-related macular degeneration (AMD), including dry and wet (non-exudative and exudative) AMD, choroidal neovascularization (CNV), Macular Telangiectasia, uveitis, diabetic and other ischemia-related neovascular-related retinopathies, or cellular degenerative diabetic macular edema, pathological myopia, von Hippel-Lindau disease, histoplasmosis of the eye, Doyne honeycomb retinal dystrophy/Malattia Leventinese, Stargarts disease, Glucoma, Central Retinal Vein Occlusion (CRVO), BRVO, corneal neovascularization, retinal neovascularization.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound that possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N methylglucamine, and the like. In certain embodiments, a pharmaceutically acceptable salt is the hydrochloride salt. In certain embodiments, a pharmaceutically acceptable salt is the sodium salt.

"Pharmaceutically acceptable excipient" refers to a pharmaceutically acceptable diluent, a pharmaceutically acceptable adjuvant, a pharmaceutically acceptable vehicle, a pharmaceutically acceptable carrier, or a combination of any of the foregoing with which a compound provided by the present disclosure can be administered to a patient, which does not destroy the pharmacological activity thereof and which is non-toxic when administered in doses sufficient to provide a therapeutically effective amount of the compound or a pharmacologically active metabolite thereof.

"Treatment" is an administration of at least one therapeutic agent for preventing the development or altering the pathology of a disorder. Accordingly, treatment refers to both therapeutic treatment and prophylactic or preventative measures. Those in need of treatment include those already with the disorder as well as those in which the disorder is to be prevented. As disclosed herein, the preferred agent for administration comprises at least one of the disclosed anti-C5 antibodies. In treatment of a complement related disease, the therapeutic agent, comprising at least one of the presently disclosed antibodies or a coding sequence for such antibody, may directly or indirectly alter the magnitude of response of a component of the complement pathway, or render the disease more susceptible to treatment by other therapeutic agents, e.g., antibiotics, antifungals, anti-inflammatory agents, chemotherapeutics, etc.

"Therapeutically effective amount" refers to the amount of an agent that, when administered to a subject for treating a disease, or at least one of the clinical symptoms of a disease, is sufficient to effect such treatment of the disease or symptom thereof. The specific therapeutically effective amount may vary depending, for example, on the agent, the disease and/or symptoms of the disease, severity of the disease and/or symptoms of the disease, the age, weight, and/or health of the patient to be treated, and the judgment of the prescribing physician. An appropriate amount in any given compound can be ascertained by those skilled in the art and/or is capable of determination by routine experimentation.

"Therapeutically effective dose" refers to a dose that provides effective treatment of a disease in a patient. A therapeutically effective dose may vary from agent to agent and/or from patient to patient, and may depend upon factors such as the condition of the patient and the severity of the disease. A therapeutically effective dose can be determined in accordance with routine pharmacological procedures known to those skilled in the art.

"Pathology" of a disease, such as a complement-associated eye condition, includes all phenomena that compromise the well-being of the patient. This includes, without limitation, abnormal or uncontrollable cell growth, protein production, abnormal or uncontrolled cell death, auto-antibody production, complement production, complement activation, MAC formation, interference with the normal functioning of neighboring cells, release of cytokines or other secretory products at abnormal levels, suppression or aggravation of any inflammatory or immunological response, infiltration of inflammatory cells into cellular spaces, edema etc.

"Mammal" as used herein refers to any animal classified as a mammal, including, without limitation, humans, higher primates, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

The present disclosure provides antibodies that bind complement Component 5 protein. Specifically, disclosed herein are antibodies that bind C5 and C5b, but not C5a. The presently disclosed antibodies do not inhibit C5 cleavage, but do inhibit MAC formation and MAC-dependent cell lysis.

The antibodies described herein comprise a scaffold structure with one or more Complementarity Determining Regions (CDRs). In certain embodiments, the CDRs include no more than two amino acid additions, deletions, or substitutions from one or more of the heavy chain CDR1, CDR2, and CDR3, and the light chain CDR1, CDR2 and CDR3 of a parent sequence, for example SEQ ID NOs:13-48.

In other embodiments, the CDRs are defined by a consensus sequence having common conserved amino acid sequences and variable amino acid sequences as described herein.

In certain embodiments, the scaffold structure of the C5 antibodies of the disclosure can be based on antibodies, including, but not limited to, monoclonal antibodies, bispecific antibodies, minibodies, domain antibodies, synthetic antibodies (e.g. antibody mimetics), chimeric antibodies, humanized antibodies, antibody fusions (e.g. antibody conjugates), and fragments of each, respectively. The various structures are further described and defined hereinbelow. In some embodiments, the scaffold structures comprise one or more of SEQ ID NOs:1-12. In certain embodiments, the scaffold sequences include one or more amino acid additions, deletions, or substitutions compared to SEQ ID NOs: 1-12.

The anti-C5 antibodies are useful in treating consequences, symptoms, and/or the pathology associated with complement activation. These include, but are not limited to, atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, cerebral malaria, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation leukopheresis, plasmapheresis, heparin-induced extracorporeal membrane oxygenation LDL precipitation, extracorporeal membrane oxygenation and the like.

Other uses for the disclosed antibodies include, for example, diagnosis of complement- and C5-associated diseases.

Aspects of the present disclosure provide anti-C5 antibodies, particularly antibodies that include at least one CDR including heavy chain and/or light chain CDRs, as more fully described below, or combinations thereof.

In one aspect, the anti-C5 antibodies inhibit activity of C5 and/or C5b, and inhibit the ability of C5b to form protein complexes. Without being held to a particular mechanism or theory, in some embodiments the antibodies interrupt the complement pathway, thereby interrupting the complement cascade, formation of the MAC, and cell lysis. This disruption may prevent or alter disease course in, but is not limited to, geographic atrophy and exudative AMD, uveitis, diabetic and other neovascular or ischemia-related retinopathies, diabetic macular edema, pathological myopia, von Hippel-Lindau disease, histoplasmosis of the eye, Retinal Angiomatous Proliferation, Central Retinal Vein Occlusion (CRVO), Branched Retinal Vein Occlusion (BRVO), corneal neovascularization, retinal neovascularization, and the like. In some embodiments, the anti-C5 antibody may inhibit C5b initiation of MAC formation.

The antibodies of the disclosure thus may serve to identify conditions related to C5 or the complement system or related diseases or conditions. In addition, the antibodies can be used to regulate and/or suppress effects mediated by C5 and/or other, downstream, complement proteins, as such having efficacy in the treatment and prevention of various diseases and conditions associated with complement and/or C5.

More specifically, the disclosure provides anti-C5 antibodies and polynucleotides that encode them. In various aspects, the anti-C5 antibodies inhibit at least one of the biological responses mediated by C5, C5b and/or other complement proteins, and as such can be useful for ameliorating the effects of complement-associated and C5-associated diseases and disorders. Also provided by the disclosure are expression systems, including mammalian cell lines and bacterial cells, for the production of anti-C5 antibodies and methods of treating diseases associated with complement activation.

The antibodies of the present disclosure comprise a scaffold structure and one or more complementary determining regions (CDRs) that bind to C5. In various embodiments, the antibody comprises a first and/or second amino acid sequence.

In one embodiment, the first and/or the second amino acid sequence comprises a sequence selected from the group consisting of SEQ ID NOs:1-48.

In various embodiments, the antibodies can include one or both of the first and second amino acid sequences. The first and second amino acid sequences can be a single linear amino acid sequence, can be covalently bonded by disulfide bridges, or can be non-covalently bonded.

Complement Component 5, C5

The membrane attack complex (MAC) is typically formed as a result of the activation of one or more of the three principal pathways, eg the alternative pathway, Lectin pathway or classical pathway of the complement system or through alterations in C5 confirmation or activation by the less common extrinsic pathway. MAC is one of the effector proteins of the immune system and forms transmembrane channels. These channels disrupt the phospholipid bilayer of target cells, leading to cell lysis and death. A critical protein in the assembly of the MAC is C5. C5 has a molecular weight of about 190 kDa (about 1600 aa) and consists of two polypeptide chains, the alpha chain (a, 115 kDa) and the beta chain ($\beta$, 75 kDa). The alpha and beta chains are connected by disulfide bonds. C5 convertase cleaves C5 at an arginine, 75 residues downstream from the N-terminus of the alpha-chain. This cleavage releases the small C5a fragment (approximately 77-74 aa in length and about 11 kDa), which is a potent inflammatory molecule. The C5 convertase cleavage also results in activation of C5b, which can then initiate formation of the membrane attack complex (MAC). The C5b protein consists of the alpha chain (now 104 kDa) and the beta chain (75 kDa).

Figure 2:
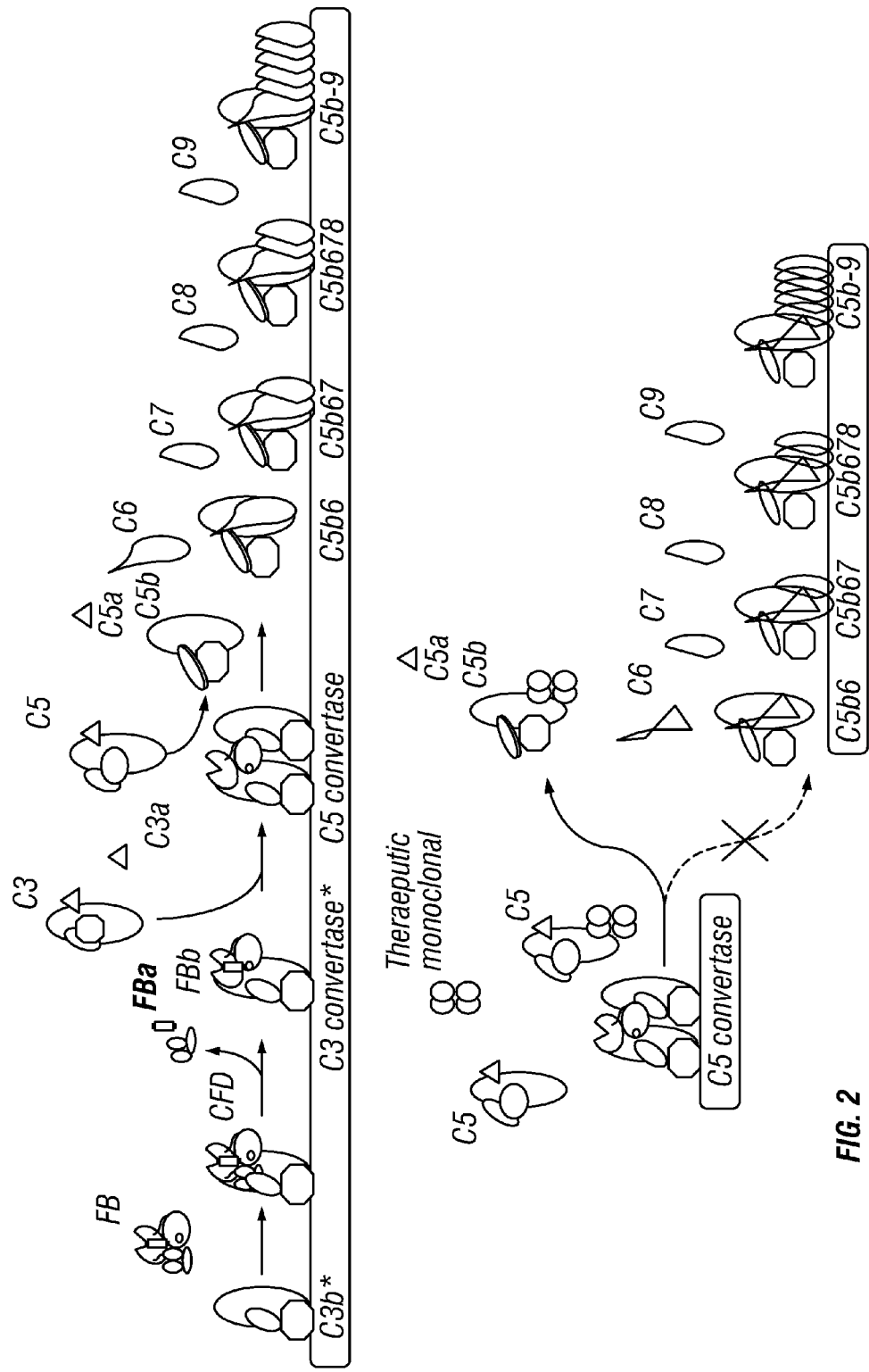
FIG. 2 shows a schematic of MAC formation and shows the mechanism of a monoclonal antibody therapeutic in blocking MAC but not C5a generation

Cleavage of C5 by the C5 convertase leads to the formation of C5a and C5b. The newly formed C5b fragment recruits C6, followed by the sequential addition of C7, C8 and multiple C9 molecules to assemble MAC. Active MAC has a subunit composition of C5b-C6-C7-C8-C9{n}. The ring structure formed by C9 is a pore in the membrane of the target cell. If enough pores form, the cell is no longer able to survive due to free diffusion of molecules in and out of the cell. At sublytic concentrations these pores can contribute to proinflammatory cell activation, while at lytic concentrations pore formation leads to cell death. The formation of MAC is schematically shown in FIG. 2. Both C5a and C5b are proinflammatory molecules. C5a binds the C5a receptor (C5aR) and stimulates the synthesis and release from human leukocytes of proinflammatory cytokines such as TNF-alpha, IL-1 beta, IL-6 and IL-8. C5a has also been shown to be associated with tissue homeostasis (removal of opsinized particles), neural survival and promotion of anti-angiogenic response. Most anti-C5 antibodies inhibits the formation of C5a and C5b, which would not only interfere with the activation of MAC by blocking C5b formation, but would also detrimentally block C5a activity, which may contribute to maintenance of retinal health. What is needed is an antibody that selectively blocks C5b so it inhibits MAC formation, while preserving the actions of C5a.

Reducing the formation of C5b may aid in treating many diseases of the complement system as well as inflammatory diseases. One such disease is age-related macular degeneration or AMD. AMD is a medical condition that results in a loss of vision, due to deterioration of the retina. The complement system has been implicated in AMD through a strong association between several genes in the complement system and a person's risk of developing AMD. Thus, inhibiting the complement system through prevention of C5b protein incorporation in the MAC may be critical to the therapeutic treatment of AMD.

Anti-C5 Antibodies

In one aspect, the disclosure provides antibodies that bind C5, do not bind C5a, and do not inhibit the formation of C5a. In certain aspects, the disclosure provides recombinant antibodies that bind C5, i.e. anti-C5 antibodies. In this context, recombinant antibodies can be produced using recombinant techniques, i.e., through the expression of a recombinant nucleic acid as described below. Methods and techniques for the production of recombinant proteins are well known in the art.

In some embodiments, the antibodies of the disclosure are isolated or purified. An isolated or purified antibody can be unaccompanied by at least some of the material with which it is normally associated in its natural state (contaminating material). In a one embodiment, the contaminating material constitutes less than about 50%, alternatively less than about 20%, and alternatively less than about 10% by weight of the total weight of a given sample. In some embodiments the contaminant may be protein.

In many embodiments, the purified anti-C5 antibody is produced in or from an organism other than the organism from which it is derived. In some embodiments, the anti-C5 antibody can be made at a significantly higher concentration than is normally seen, through the use of an inducible promoter or high expression promoter, such that the antibody is made at increased concentration levels.

In some embodiments, the isolated or purified antibody can be removed from components that can interfere with diagnostic and/or therapeutic uses for the antibody. In some embodiments, the antibody will be purified to greater than 90% by weight of antibody, wherein the total protein concentration is determined, for example by the Lowry method, and the percent antibody concentration is determined by a visual method, such as a protein gel. In one embodiment the anti-C5 antibody is more than 99% by weight, for example pure enough to obtain at least 15 residues of N-terminal or internal amino acid sequence by use of a common amino acid sequencing technique (e.g. Edman degradation and mass spectrometry), or to homogeneity by SDS-PAGE under reducing or nonreducing conditions using Coomassie blue or silver stain. Isolated antibodies include antibodies in situ within recombinant cells since at least one component of the antibody's natural environment will not be present. Ordinarily, however, isolated antibody will be prepared by at least one purification step.

The disclosed antibody can bind specifically to C5 and can be used to inhibit or modulate the biological activity of C5 and C5b. In certain embodiments, the disclosed antibodies are created by immunization of an animal, in other cases antibodies can be produced by recombinant DNA techniques. In additional embodiments, anti-C5 antibodies can be produced by enzymatic or chemical cleavage of traditional antibodies (traditional antibodies may be synonymous with human antibodies). In some embodiments, the antibody can comprise a tetramer. In some of these embodiments, each tetramer is typically composed of two identical pairs of polypeptide chains, each pair having one light chain (typically having a molecular weight of about 25 kDa) and one heavy chain (typically having a molecular weight of about 50-70 kDa). The amino-terminal portion of each chain includes a variable region of about 100 to 110 or more amino acids and can be responsible for antigen recognition. The carboxy-terminal portion of each chain can define a constant region, which is primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4.

Some antibodies, for example antibodies found in camels and llamas, can be dimers consisting of two heavy chains and include no light chains. Muldermans et al., 2001, *J. Biotechnol.* 74:277-302; Desmyter et al., 2001, *J. Biol. Chem.* 276:26285-26290. Crystallographic studies of camel antibodies have revealed that the CDR3 regions of these antibodies form a surface that interacts with the antigen and thus is critical for antigen binding like in the more typical tetrameric antibodies. The disclosure encompasses dimeric antibodies consisting of two heavy chains, or fragments thereof that can bind to and/or inhibit the biological activity of C5 and/or C5b.

The antibodies of the disclosure specifically bind to human C5. An antibody can specifically bind to C5 when the antibody has a higher binding affinity for that C5 than for any other antigen or protein. In various embodiments, the binding affinity is measured by determining an equilibrium binding constant, for example a $K_d$ (or Kd), or $K_a$ (or Ka). In some embodiments the disclosed antibody binds to a target antigen with a Kd from about $10^{-7}$ M to about $10^{-13}$ M, or from about $10^{-9}$ M to about $10^{-12}$ M, or from about $10^{-11}$ M to about $10^{-12}$ M. In various embodiments, the Kd is less than about $10^{-8}$ M, $10^{-9}$ M, $10^{-10}$ M, $10^{-11}$ M or $10^{-12}$ M, and more than about $10^{-13}$ M, $10^{-12}$ M, $10^{-11}$ M, $10^{-10}$ M, $10^{-9}$ M.

In some cases the Kd for the other antigen is greater than 1× the target antigen Kd, greater than 2× the target antigen Kd, greater than 3× the target antigen Kd, greater than 4× the target antigen Kd, greater than 5× the target antigen Kd, greater than 6× the target antigen Kd, greater than 7× the target antigen Kd, greater than 8× the target antigen Kd, greater than 9× the target antigen Kd, greater than 10× the target antigen Kd (for example where the Kd of the antibody is $X^{-09}$ M for the target antigen, the Kd of the antibody for another antigen can be 10× greater, or $X^{-08}$ M), or greater than 100× (for example where the Kd of the antibody is $X^{-10}$ M for the target antigen, the Kd of the antibody for another antigen can be 10× greater, or $X^{-08}$ M). In some cases, the equilibrium binding constant can be expressed as an equilibrium association constant, $K_a$ or Ka.

The equilibrium binding constant can be determined using various methods. In some cases, an equilibrium binding constant for the disclosed antibody is determined by measuring on ($k_1$) and off ($k_{-1}$) rates in a protein binding assay. One exemplary method of determining the equilibrium binding constant is by Bio-Layer Interferometry (BLI). BLI is a label-free technology capable of determining binding kinetics in solution. In one exemplary method, an antibody can be a human IgG, and the anti-C5 antibody can be captured by an Anti-human IgG Fc capture (AHC) biosensor tips (ForteBio, Menlo Park, Calif., USA) according to the manufacturers directions. Other types of protein binding assays include: Co-immunoprecipitation; Bimolecular fluorescence complementation; Affinity electrophoresis; Pull-down assays; Label transfer; The yeast two-hybrid screen; Phage display; in vivo crosslinking of protein complexes using photo-reactive amino acid analogs; Tandem affinity purification; Chemical cross-linking; Chemical cross-linking followed by high mass MALDI mass spectrometry; SPINE (Strepprotein interaction experiment); Quantitative immunoprecipitation combined with knock-down; Proximity ligation assay Bio-Layer Interferometry; Dual polarisation interferometry; Static light scattering; Dynamic light scattering; Surface plasmon resonance; Fluorescence polarization/anisotropy; fluorescence correlation spectroscopy; Fluorescence resonance energy transfer; Protein activity determination by NMR multi-nuclear relaxation measurements, or 2D-FT NMR spectroscopy in solutions, combined with nonlinear regression analysis of NMR relaxation or 2D-FT spectroscopy data sets; Protein—protein docking; Isothermal Titration calorimetry; and, Microscale Thermophoresis.

In embodiments where the anti-C5 antibody is used for therapeutic applications, one characteristic of an anti-C5 antibody is that it can modulate and/or inhibit one or more biological activities of, or mediated by C5. In this case, the antibody can bind specifically to C5, can substantially modulate the activity of C5 and/or C5b, and/or can inhibit the binding of C5b to other proteins (e.g. C6, C7).

In many embodiments, C5 activity, and the antibody's ability to inhibit that activity, is measured by analyzing lysis of red blood cells in the presence of 10% human serum. Activation of the alternative pathway of (AP) requires higher concentrations of serum than the classical pathway. Generally, a final concentration of 5 mM $Mg^{++}$ in the presence of 5 mM EGTA is used in the assays where the EGTA chelates $Ca^{++}$ preferentially. The AP of most mammalian species is activated spontaneously by rabbit erythrocytes so they are a convenient target. Prepare rabbit erythrocytes (Complement Technology, Inc.) by washing 3 times with GVB° (CompTech product) and re-suspending into $5 \times 10^8$/ml. Different amount of anti-factor C5 antibody was diluted with GVB°. Mix the 100 ul reaction on ice in the order of serial diluted anti-factor Bb antibody, 0.1M MgEGTA (CompTech product), ½NHS (normal human serum diluted ½ with GVB°), and rabbit Er. Then, incubate the reaction at 37° C. for 30 minutes on a shaker. Add 1.0 ml cold GVBE. Mix and centrifuge for 3 min at approx. 1000×g, or higher, to pellet cells. Transfer 100 ul of the supernatant to a 96-well plate and read at 412 nm (SoftMax Pro 4.7.1). Data was analyzed using GraphPad Prism 4.

Not every antibody that specifically binds to an antigen can block antigen binding to its normal ligand and thus inhibit or modulate the biological effects of the antigen. As is known in the art, such an effect can depend on what portion of the antigen the antibody binds, and on both the absolute and the relative concentrations of the antigen and the antibody, in this case, a C5 antibody. To be considered capable of inhibiting or modulating the biological activity of C5 and/or C5b, as meant herein, an antibody can be able, for example, to inhibit the human serum mediated hemolysis by at least about 20%, 40%, 60%, 80%, 85%, 90%, 95%, 99%, or more.

The concentration of an antibody required to inhibit C5 and/or C5b activity can vary widely and may depend upon how tightly the antibody binds to C5 and/or C5b. For example, one molecule or less of an antibody per molecule of C5 can be sufficient to inhibit biological activity. In some embodiments, a ratio of C5:anti-C5 antibody of about 1,000:1 to about 1:1,000, including about 2:1, 1:1, 1:2, 1:4, 1:6, 1:8, 1:10, 1:20, 1:40, 1:60, 1:100, 1:500, 1:1,000 or more can be required to inhibit the biological activity of C5. In many cases, the ability to inhibit C5 activity may depend upon the concentration of C5 and/or the concentration of anti-C5 antibody.

In some embodiments, the antibodies of the disclosure comprise (a) a scaffold, and (b) one or more CDRs, which are regions that are determinative of antigen binding specificity and affinity. Complementary Determining Regions or CDRs are regions of an antibody that constitutes the major surface contact points for antigen binding. One or more CDRs are embedded in the scaffold structure of the antibody. The scaffold structure of the antibodies of the disclosure can be an antibody, or fragment or variant thereof, or can be completely synthetic in nature. The various scaffold structures of the antibodies of the disclosure are further described below.

In an embodiment of the presently disclosed antibodies, the antibody can be a variant antibody having an amino acid sequence with at least 75% amino acid sequence identity, homology, or similarity with the amino acid sequence of a parent amino acid sequence. For example, in some embodiments the heavy or light chain variable domain sequence of the variant antibody is 75% identical to the heavy or light chain variable domain sequence of a parent sequence, alternatively at least 80%, alternatively at least 85%, alternatively at least 90%, and alternatively at least 95%. In most cases, the variant antibody will have few or no changes in the CDR sequence, and therefore, in most cases, will bind the target antigen with a similar affinity. Identity or similarity with respect to this sequence is defined herein as the percentage of amino acid residues in the variant sequence that are identical (i.e. same residue) or similar (i e amino acid residue from the same group based on common side-chain properties, see below) with the parent antibody amino acid sequence, after aligning the sequences and introducing gaps, if necessary, to achieve the maximum percent sequence identity.

CDRs

The antibodies of the disclosure include scaffold regions and one or more CDRs. An antibody of the disclosure may have between one and six CDRs (as typically do naturally occurring antibodies), for example, one heavy chain CDR1 ("HC CDR1" or "CDRH1"), and/or one heavy chain CDR2 ("HC CDR2" or "CDRH2"), and/or one heavy chain CDR3 ("HC CDR3" or "CDRH3"), and/or one light chain CDR1 ("LC CDR1" or "CDRL1"), and/or one light chain CDR2 ("LC CDR2" or "CDRL2"), and/or one light chain CDR3 ("LC CDR3" or "CDRL3"). The term "naturally occurring" as used throughout the specification in connection with biological materials such as polypeptides, nucleic acids, host cells, and the like, refers to materials which are found in nature. In naturally occurring antibodies, a heavy chain CDR1 typically comprises about five (5) to about seven (7) amino acids, a heavy chain CDR2 typically comprises about sixteen (16) to about nineteen (19) amino acids, and a heavy chain CDR3 typically comprises about three (3) to about twenty five (25) amino acids. CDR1 of the light chain typically comprises about ten (10) to about seventeen (17) amino acids, the light chain CDR2 typically comprises about seven (7) amino acids, and the light chain CDR3 typically comprises about seven (7) to about ten (10) amino acids.

Amino acids of the present disclosure include natural and synthetic amino acids (e.g., homophenylalanine, citrulline, ornithine, and norleucine). Such synthetic amino acids can be incorporated, in particular when the antibody is synthesized in vitro by conventional methods well known in the art. In addition, any combination of peptidomimetic, synthetic and naturally occurring residues/structures can be used Amino acid includes imino acid residues such as proline and hydroxyproline. The amino acid "R group" or "side chain" can be in either the (L)- or the (S)-configuration. In a specific embodiment, the amino acids are in the (L)- or (S)-configuration. In some embodiments, the amino acids can form peptidomimetic structures, i.e., peptide or protein analogs, such as peptoids (see, Simon et al., 1992, Proc. Natl. Acad. Sci. U.S.A. 89:9367, incorporated by reference herein), which can be resistant to proteases or other physiological and/or storage conditions.

The structure and properties of CDRs within a naturally occurring antibody are described further below. Briefly, in a traditional antibody scaffold, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). See, infra. The CDRs provided by the present disclosure, however, may not only be used to define the antigen binding domain of a traditional antibody structure, but can be embedded in a variety of other scaffold structures, as described herein.

Specific CDRs for use in the disclosed antibodies are presented in Table 1.

TABLE 1

CDR Amino Acid Sequence for Antibodies

LIGHT CHAIN VARIABLE DOMAIN CDRs

1B6

| VL CDR1 | SEQ ID NO: 13 | SSISSSN |
| VL CDR2 | SEQ ID NO: 14 | GTS |
| VL CDR3 | SEQ ID NO: 15 | QQWSSYPFT |

6C12

| VL CDR1 | SEQ ID NO: 19 | SSISSSN |
| VL CDR2 | SEQ ID NO: 20 | GTS |
| VL CDR3 | SEQ ID NO: 21 | QQWSTYPFT |

8c7

| VL CDR1 | SEQ ID NO: 25 | KSISKY |
| VL CDR2 | SEQ ID NO: 26 | SGS |
| VL CDR3 | SEQ ID NO: 27 | QQHNEYPYT |

10B11

| VL CDR1 | SEQ ID NO: 31 | SSISSNY |
| VL CDR2 | SEQ ID NO: 32 | RTS |
| VL CDR3 | SEQ ID NO: 33 | QQGSGIFT |

10G4

| VL CDR1 | SEQ ID NO: 37 | QDISSY |
| VL CDR2 | SEQ ID NO: 38 | YTS |
| VL CDR3 | SEQ ID NO: 39 | QQGNVFPWT |

TABLE 1 -continued

CDR Amino Acid Sequence for Antibodies

10C9

| VL CDR1 | SEQ ID NO: 43 | QDVNTA |
| VL CDR2 | SEQ ID NO: 44 | WAS |
| VL CDR3 | SEQ ID NO: 45 | QQHHVSPWT |

HEAVY CHAIN VARIABLE DOMAIN CDRs

1B6

| VH CDR1 | SEQ ID NO: 16 | GYTFTDYE |
| VH CDR2 | SEQ ID NO: 17 | IDPETGGA |
| VH CDR3 | SEQ ID NO: 18 | TRLGSSPWYFDV |

6C12

| VH CDR1 | SEQ ID NO: 22 | GYTFTDYE |
| VH CDR2 | SEQ ID NO: 23 | IDPETGGT |
| VH CDR3 | SEQ ID NO: 24 | TRLGISPWYFDV |

8c7

| VH CDR1 | SEQ ID NO: 28 | GYRFTDYN |
| VH CDR2 | SEQ ID NO: 29 | ISPNNGGT |
| VH CDR3 | SEQ ID NO: 30 | ARREAWYGGYYKWYFDV |

10B11

| VH CDR1 | SEQ ID NO: 34 | GYTFTTYG |
| VH CDR2 | SEQ ID NO: 35 | INTYSGVP |
| VH CDR3 | SEQ ID NO: 36 | ARRDFYGNYGDY |

10G4

| VH CDR1 | SEQ ID NO: 40 | GYTFTDSY |
| VH CDR2 | SEQ ID NO: 41 | ILPNNGGI |
| VH CDR3 | SEQ ID NO: 42 | ARSGGLVGGYFDY |

10C9

| VH CDR1 | SEQ ID NO: 46 | GYTFTDEY |
| VH CDR2 | SEQ ID NO: 47 | INPNNGGA |
| VH CDR3 | SEQ ID NO: 48 | ARLGYSNPYFDF |

In another embodiment, the disclosure provides an antibody that binds C5, wherein said antibody comprises at least one HC CDR region having no more than two (2) amino acid additions, deletions or substitutions of any of SEQ ID NOs:16-18, 22-24, 28-30, 34-36, 40-42, and 46-48 and/or at least one LC CDR region having no more than two (2) amino acid additions, deletions or substitutions of any of SEQ ID NOs:13-15, 19-21, 25-27, 31-33, 37-39, and 43-45. Embodiments of various heavy chain and light chain variable regions of the disclosure are depicted in TABLE 2 and SEQ ID NOs:1-12. In some embodiments, of particular use are antibodies with a HC CDR3 and/or LC CDR3 region. Additionally, in some embodiments antibodies can have one CDR having no more than two (2) amino acid additions, deletions or substitutions of the sequence selected from the HC CDR regions of any of SEQ ID NOs:16-18, 22-24, 28-30, 34-36, 40-42, and 46-48 and a LC CDR having no more than two (2) amino acid additions, deletions, or substitutions of any of SEQ ID NOs:13-15, 19-21, 25-27, 31-33, 37-39, and 43-45 (e.g., the antibody has two CDR regions, one HC CDR and one LC CDR, a specific embodiment are antibodies with both a HC CDR3 and a LC CDR3, for example, SEQ ID NOs:45 and 48).

TABLE 2

Light Chain Sequences

SEQ ID NO: 1, L1
DIVLTQSPDSLAVSLGERATINCKASQDVNTAVAWYQQKPDQSPKLLIYWASTRHTG
VPARFTGSGSGTDYTLTISSLQAEDVAVYFCQQHHVSPWTFGGGTKVEIK

SEQ ID NO: 3, L2
DIVLTQSPATLSLSPGERATLSCRASQDVNTAVAWYQQKPDQSPKLLIYWASTRHTG
VPARFTGSGSGTDYTLTISSLQPEDFAVYFCQQHHVSPWTFGGGTKVEIK

SEQ ID NO: 5, L3
DIVLTQSPSFLSASVGDRVTITCQASQDVNTAVAWYLQKPGKSPKLLIYWASTRHTG
VPARFTGSGSGTDYTLTISSLQPEDFAVYFCQQHHVSPWTFGGGTKVEIK

SEQ ID NO: 7, L4
DIVLTQSPATLSLSPGERATLSCRASQDVNTAVAWYQQKPGKSPKLLIYWASTRHTG
VPARFTGSGSGTDYTLTISSLQPEDFAVYFCQQHHVSPWTFGGGTKVEIK

SEQ ID NO: 9, L5
DIVLTQSPATLSLSPGERATLSCRASQDVNTAVAWYQQKPGQSPKLLIYWASTRHTG
VPARFTGSGSGTDYTLTISSLQSEDFAVYFCQQHHVSPWTFGGGTKVEIK

SEQ ID NO: 11, L6
DIVLTQSPSFLSASVGDRVTITCQASQDVNTAVAWYQQKPGKSPKLLIYWASTRHTG
VPARFTGSGSGTDYTLTISSLQPEDFAVYFCQQHHVSPWTFGGGTKVEIK

Heavy Chain Sequences

SEQ ID NO: 2, H1
QVQLVQSGAEVKKPGASVKVSCKASGYTFTDEYMNWVRQAPGQSLEWMGYINPN
NGGADYNQKFQGRVTMTVDQSISTAYMELSRLRSDDTAVYFCARLGYSNPYFDFW
GQGTLVTVSS

SEQ ID NO: 4, H2
EVQLVQSGAEVKKPGASVKVSCKASGYTFTDEYMNWVRQAPGKSLEWVGYINPNN
GGADYNQKFQGRVTITVDQSASTAYMELSSLRSEDTAVYFCARLGYSNPYFDFWGQ
GTLVTVSS

SEQ ID NO: 6, H3
QVQLVQSGAEVKKPGASVKVSCKASGYTFTDEYMNWVRQAPGQSLEWMGYINPN
NGGADYNPSLKSRVTISVDQSISTAYMELSRLRSDDTAVYFCARLGYSNPYFDFWGQ
GTLVTVSS

SEQ ID NO: 8, H4
EVQLVESGGGLVKPGGSLRLSCAASGYTFTDEYMNWVHQAPGKSLEWVGYINPNN
GGADYNPSLKSRVTISVDQSKSIAYLQMNSLKTEDTAVYFCARLGYSNPYFDFWGQ
GTLVTVSS

SEQ ID NO: 10, H5
QVQLKQSGAEVKKPGASVKVSCKASGYTFTDEYMNWVRQAPGKSLEWMGYINPN
NGGADYNQKFQGRVTMTVDQSISTAYMELSRLRSDDTAVYFCARLGYSNPYFDFW
GQGTLVTVSS

SEQ ID NO: 12, H6
QVQLVQSGSELKKPGASVKVSCKASGYTFTDEYMNWVRQAPGKSLEWMGYINPNN
GGADYNQKFQGRVTMTVNQSISTAYMELSRLRSDDTAVYFCARLGYSNPYFDFWG
QGTLVTVSS

Variant CDR Sequences

In another embodiment, the disclosure provides an antibody that binds a C5 protein, wherein said antibody comprises at least one HC CDR region having no more than two (2) amino acid additions, deletions or substitutions of any HC CDR1, HC CDR2, or HC CDR3 region (as discussed above) of SEQ ID NOs:16-18, 22-24, 28-30, 34-36, 40-42, and 46-48 and/or at least one LC CDR region having no more than two (2) amino acid additions, deletions or substitutions of any LC CDR1, LC CDR2, or LC CDR3 region (as discussed above) of SEQ ID NOs:13-15, 19-21, 25-27, 31-33, 37-39, and 43-45. In this embodiment, of particular use are antibodies with a HC CDR3 or LC CDR3 region. Additional embodiments utilize antibodies with one CDR having no more than 2 amino acid additions, deletions or substitutions of the sequence selected from the HC CDR regions of any of SEQ ID NOs:16-18, 22-24, 28-30, 34-36, 40-42, and 46-48 and a LC CDR region having no more than two (2) amino acid additions, deletions or substitutions of any of SEQ ID NOs:13-15, 19-21, 25-27, 31-33, 37-39, and 43-45 (e.g., the antibody has two CDR regions, one HC CDR and one LC CDR, a specific embodiment are antibodies with both a HC CDR3 and a LC CDR3 region, for example SEQ ID NO:45 and 48).

As will be appreciated by those in the art, for any antibody with more than one CDR from the depicted sequences, any combination of CDRs independently selected from the depicted sequences is useful. Thus, antibodies with one, two, three, four, five or six independently selected CDRs can be generated. However, as will be appreciated by those in the art, specific embodiments generally utilize combinations of CDRs that are non-repetitive, e.g., antibodies are generally not made with two HC CDR2 regions, etc.

A further aspect of the disclosure provides for an isolated antibody that binds C5 where the isolated antibody comprises a heavy chain amino acid sequence having no more than two (2) amino acid additions, deletions or substitutions of any of SEQ ID NOs:16-18, 22-24, 28-30, 34-36, 40-42, and 46-48, and a light chain amino acid sequence having no more than two (2) amino acid additions, deletions or substitutions of any of SEQ ID NOs:13-15, 19-21, 25-27, 31-33, 37-39, and 43-45. It is noted that any of the heavy chain sequences can be mixed and matched with any of the light chain sequences.

Generally, the amino acid homology, similarity, or identity between individual variant CDRs, described herein, is at least 80% when compared to the sequences disclosed herein. In many cases the aa homology, similarity, or identity is at least 85%, 90%, 91%, 92%, 93%, 94%, 95%, 96%, 97%, 98%, and 99%.

Sequence Identity/Homology

As is known in the art, a number of different programs can be used to identify the degree of sequence identity or similarity a protein or nucleic acid has to a second sequence.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, using the default settings, or by inspection. Percent identity can be calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values for proteins: overlap span=1, overlap fraction=0.125, word threshold, T=11. The HSP S and HSP S2 parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs or variable regions are at least 80% to the sequences, or alternatively increasing homologies or identities of at least 85%, 90%, 91%, 92%, 93%, 94%, 95%, 96%, 97%, 98%, 99%, and almost 100%.

In a similar manner, percent (%) nucleic acid sequence identity, with respect to the nucleic acid sequences that encode the disclosed antibodies, is the percentage of nucleotide residues in a candidate sequence that are identical with the nucleotide residues in the coding sequence of the antibody. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and variant variable domain sequences are at least 80%, and alternatively with increasing homologies or identities of at least 85%, 85%, 90%, 91%, 92%, 93%, 94%, 95%, 96%, 97%, 98%, 99%, and almost 100%. In many cases non-identical nucleic acid sequences, because of the degeneracy of the genetic code, can code for the same amino acid sequence.

Homology between nucleotide sequences is often defined by their ability to hybridize to each other. In some embodiments, selective hybridization can refer to binding with high specificity. Polynucleotides, oligonucleotides and fragments thereof in accordance with the disclosure selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein.

The stringency of hybridization reactions is readily determinable by one of ordinary skill in the art, and generally is an empirical calculation dependent upon probe length, probe concentration/composition, target concentration/composition, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

High stringency conditions are known in the art; see, for example Sambrook et al., 2001, supra, and *Short Protocols in Molecular Biology*, Second Edition, Ausubel et al. eds., John Wiley & Sons, 1992, both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, *Techniques In Biochemistry and Molecular Biology—Hybridization with Nucleic Acid Probes*, "Overview of principles of hybridization and the strategy of nucleic acid assays" (1993).

In some embodiments, stringent or high stringency conditions can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42C; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium Ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions can be used, as are known in the art; see, Sambrook et al., 2001, supra; Ausubel et al., 1992, supra, and Tijssen, 1993, supra.

In some cases, moderately stringent conditions can include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In some embodiments, the disclosed antibodies and variants thereof can be prepared by site specific mutagenesis of nucleotides within a DNA sequence encoding the antibody. This can be achieved using cassette or PCR mutagenesis or other techniques well known in the art, to produce DNA encoding the variant, and thereafter expressing the recombinant DNA in cell culture as outlined herein. In some cases, antibody fragments comprising variant CDRs having up to about 100-150 residues can be prepared by in vitro synthesis using established techniques. These variant fragments can exhibit the same qualitative biological activity as the naturally occurring analogue, e.g., binding to C5 and inhibiting complement, although variants can also be selected which have modified characteristics as will be more fully outlined below.

While the site or region for introducing an amino acid sequence variation is predetermined, the mutation per se need not be predetermined. For example, in order to optimize a mutation at a given site, random mutagenesis can be conducted at the target codon or region and the expressed antibody CDR or variable region sequence variants screened for the optimal desired antibody activity. Techniques for making substitution mutations at predetermined sites in DNA having a known sequence are well known, for example, M13 primer mutagenesis and PCR mutagenesis. Screening of the mutants is done using assays of antibody activities, such as C5 binding.

Amino acid substitutions are typically of single residues; insertions usually will be on the order of from about one (1) to about twenty (20) amino acid residues, although considerably larger insertions can be tolerated. Deletions range from about one (1) to about twenty (20) amino acid residues, although in some cases deletions can be much larger.

Substitutions, deletions, insertions or any combination thereof can be used to arrive at a final derivative or variant. Generally these changes are done on a few amino acids to minimize the alteration of the molecule, particularly the immunogenicity and specificity of the antibody. However, larger changes can be tolerated in certain circumstances. Conservative substitutions are generally made in accordance with the following chart depicted as Table 3.

TABLE 3

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |
| Ala | Ser |

Changes in function or immunological identity can be made by selecting substitutions that are less conservative than those shown in Table 3. For example, substitutions can be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the disclosed C5 antibody, as needed. Alternatively, a variant can be selected wherein the biological activity of the disclosed antibody is altered. For example, glycosylation sites can be altered or removed as discussed herein.

Disclosed herein are polypeptide sequences homologous to SEQ ID NOs:1-48. Polypeptides disclosed herein can include amino acid sequences that are identical to the disclosed amino acid sequences. In other cases, the claimed polypeptides include amino acid sequences that can comprise conservative amino acid substitutions as compared to the disclosed sequence. Conservative amino acid substitutions can include amino acids that share characteristics with the substituted amino acid. In various cases, conservative substitution can be made without significant change in the structure or function of the polypeptide.

Conservative amino acid substitutions can be made on the basis of relative similarity of side-chain, size, charge, hydrophobicity, hydrophilicity, isoelectric point, etc. In various cases, substitutions can be assayed for their effect on the function of the protein by routine testing. Conserved amino acid substitutions include amino acids with similar hydrophilicity value, as wherein amino acids have a hydropathic index which can be based upon an amino acid's hydrophobicity and charge. In various cases, conserved amino acid substitutions can be made between amino acids of the same class, for example non-polar amino acids, acidic amino acids, basic amino acids, and neutral amino acids. Conservative substitutions can also be based upon size or volume. Amino acids can also be classified based upon their ability to form or break a given structure, such as an alpha helix, beta sheet, or intra- or inter-molecular interaction. In various cases conservative amino acid substitutions are based upon more than one characteristic.

Currently disclosed polypeptides can include both natural and non-natural amino acids. In various cases, natural amino acid side chains can be substituted with non-natural side chains. In various cases, amino acids can be derivatised.

The disclosed polypeptides include polypeptides that are homologous to the sequences of SEQ ID NOs:1-48. Homology can be expressed as % identity or % similarity or % positive. In various cases, % identity is a percentage of amino acids that are identical between two aligned polypeptides, and % similar or % positive is a percentage of amino acids that are non-identical but represent conservative substitutions. A conservative substitution may be a substitution of a like-charged amino acid, a like-sized amino acid, a like-polarity amino acid, etc. For example, lysine to arginine can be considered a conservative substitution where charge is considered.

In various cases, two polypeptides can be aligned by algorithms, for example BLASTp. In various cases, the BLASTp parameters can be set with a maximum target sequence length equal to, greater, or less than the length of the longer of the two polypeptides, the expect threshold can be set to 10, the word size to 3, and scoring matrix can be BLOSUM62, with gap costs of 11 for existence and 1 for extension. BLASTp can report homology of aligned polypeptides as "Identities" and "Positives." The aligned sequences can include gaps to achieve the alignment.

In various cases, homology of amino acid sequences can reflect the percentage of identity or positives when optimally aligned as described above. In various cases, the % homology (% positive) or % identity can be calculated by dividing the number of aligned amino acids within a comparison window. A comparison window can be the entire length of one or the other polypeptides, if the two polypeptides are of unequal length. In other cases, the comparison window can be a portion of one of the polypeptides. In various cases the comparison window for measuring homology or identity of two polypeptide sequences is greater than about 40 aa (amino acids), 45 aa, 50 aa, 55 aa, 60 aa, 65 aa, 70 aa, 75 aa, 80 aa, 85 aa, 90 aa, 95 aa, 100 aa, 150 aa, or 200 aa, and/or less than about 200 aa, 150 aa, 100 aa, 95 aa, 90 aa, 85 aa, 80 aa, 75 aa, 70 aa, 65 aa, 60 aa, 55 aa, 50 aa, or 45 aa. In some embodiment, as in the case with CDR sequences, the comparison window may be less than 40 aa, for example between less than about 25 aa, 24 aa, 23 aa, 22 aa, 21 aa, 20 aa, 19 aa, 18 aa, 17 aa, 16 aa, 15 aa, 14 aa, 13 aa, 12 aa, 11 aa, 10 aa, 9 aa, 8 aa, 7 aa, 6 aa, 5 aa, or 4 aa, and greater than about 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, or 24 aa.

In various cases, the claimed amino acid sequences can have % identity or % homology (% positive) over a given comparison window, that is greater than about 60%, 65%, 70%, 75%, 80%, 85%, 90%, 91%, 92%, 93%, 94%, 95%, 96%, 97%, 98%, or 99% and/or less than about 100%, 99%, 98%, 97%, 96%, 95%, 94%, 93%, 92%, 91%, 90%, 85%, 80%, 75%, or 70%.

In various cases, a sequence alignment can be performed using various algorithms, including dynamic, local, and global alignment. For example, the algorithm of Smith and Waterman, 1981, Adv. Appl. Math 2: 482; the alignment algorithm of Needleman and Wunsch, 1970, J. Mol. Biol. 48:443; the similarity method of Pearson and Lipman, 1988, Proc. Natl. Acad. Sci. USA 85: 2444. In various cases, computer programs can implement these algorithms (such as EMBOSS, GAP, BESTFIT, FASTA, TFASTA BLAST, BLOSUM, etc.).

In alternative cases, conserved amino acid substitutions can be made where an amino acid residue is substituted for another in the same class, for example where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In some cases, conserved amino acid substitutions can be made where an amino acid residue is substituted for another having a similar hydrophilicity value (e.g., within a value of plus or minus 2.0), where the following can be an amino acid having a hydropathic index of about −1.6 such as Tyr (−1.3) or Pro (−1.6)s are assigned to amino acid residues: Arg (+3;0); Lys (+3.0); Asp (+3.0); Glu (+3.0); Ser (+0.3); Asn (+0.2); Gin (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative cases, conserved amino acid substitutions can be made where an amino acid residue is substituted for another having a similar hydropathic index (e.g., within a value of plus or minus 2.0). In such cases, each amino acid residue can be assigned a hydropathic index on the basis of its hydrophobicity and charge characteristics, as follows: lie (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative cases, conservative amino acid changes include changes based on considerations of hydrophilicity or hydrophobicity, size or volume, or charge Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125-142, 184). Genetically encoded hydrophobic amino acids include Gly, Ala, Phe, Val, Leu, lie, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which can contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently ($C_1$-$C_6$) alkyl, substituted ($C_1$-$C_6$) alkyl, ($C_0$-$C_6$) alkenyl, substituted ($C_1$-$C_6$) alkenyl, ($C_1$-$C_6$) alkynyl, substituted ($C_0$-$C_6$) alkynyl, ($C_5$-$C_{20}$) aryl, substituted ($C_0$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp.

An non-polar or apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ala, Ile, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

A percent amino acid sequence identity value is determined by the number of matching identical residues divided by the total number of residues of the "longer" sequence in the comparison window. The "longer" sequence is the one having the most actual residues in the comparison window (gaps introduced by WU-Blast-2 to maximize the alignment score are ignored).

The alignment can include the introduction of gaps in the sequences to be aligned. In addition, for sequences which contain either more or fewer amino acids than the protein encoded by the sequence the disclosed polypeptide, it is understood that in one case, the percentage of sequence identity will be determined based on the number of identical amino acids in relation to the total number of amino acids. In percent identity calculations relative weight is not assigned to various manifestations of sequence variation, such as, insertions, deletions, substitutions, etc.

In one case, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Scaffolds

As noted herein, the antibodies of the present disclosure can comprise a scaffold structure into which the CDR(s) described above can be grafted. In one embodiment, the scaffold structure is a traditional antibody structure, that is, an antibody comprising two heavy and two light chain variable domain sequences. In some cases, the antibody combinations described herein can include additional components (framework, J and D regions, constant regions, etc.) that make up a heavy and/or a light chain. Some embodiments include the use of human scaffold components.

Accordingly, in various embodiments, the antibodies of the disclosure comprise the scaffolds of traditional antibodies. In some embodiments, the disclosed antibodies can be human and monoclonal antibodies, bispecific antibodies, diabodies, minibodies, domain antibodies, synthetic antibodies, chimeric antibodies, antibody fusions, and fragments of each, respectively. The above described CDRs and combinations of CDRs can be grafted into any of the following scaffolds.

Chimeric antibodies of the present disclosure can comprise a heavy and/or light chain sequence that is identical or homologous to the corresponding sequences derived from a particular species. For example, in one embodiment the anti-C5 antibody is a chimeric antibody comprising a human Fc domain, while the remainder of the antibody can be identical or homologous to corresponding mouse or rodent sequences. Chimeric antibodies can be fragments of such antibodies, so long as the fragments exhibit the desired biological activity and comprise sequence that is derived from another species, class of antibody, or subclass of antibody (U.S. Pat. No. 4,816,567; and Morrison et al. (1984) Proc. Natl. Acad. Sci. USA 81:6851-6855).

In some embodiments, a variable region of the presently disclosed anti-C5 antibody comprises at least three heavy chain or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), embedded within a framework region (designated framework regions 1-4, FR1, FR2, FR3, and FR4, by Kabat et al., 1991, supra; see also Chothia and Lesk, 1987, supra).

In some cases, the antibody can be comprised of a heavy chain variable domain sequence or a light chain variable domain sequence. In some cases the heavy or light chain variable domain sequence may comprise a sequence selected from the sequences of Table 1.

Traditional antibody structural units, in most cases, comprise a tetramer. Each tetramer is typically composed of two identical pairs of polypeptide chains, each pair having one light chain (typically having a molecular weight of about 25 kDa) and one heavy chain (typically having a molecular weight of about 50-70 kDa). The amino-terminal portion of each chain includes a variable region of about 100 to 110 or more amino acids primarily responsible for antigen recognition. The carboxy-terminal portion of each chain defines a constant region, while the heavy chain may comprise a total of three constant regions (CHL CH2, and CH3), wherein the constant regions may aid in regulating effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2.

Within light and heavy chains, the variable and constant regions are joined by a "J" region of about twelve (12) or more amino acids, with the heavy chain also including a "D" region of about ten (10) more amino acids. See, generally, Paul, W., ed., 1989, Fundamental Immunology Ch. 7, 2nd ed. Raven Press, N.Y. The variable regions of each light and heavy chain pair form the antibody binding site.

Some naturally occurring antibodies, for example found in camels and llamas, are dimers consisting of two heavy chains and include no light chains. Muldermans et al., 2001, *J. Biotechnol.* 74:277-302; Desmyter et al., 2001, *J. Biol. Chem.* 276:26285-26290. Crystallographic studies of a camel antibody have revealed that the CDR3 regions form a surface that interacts with the antigen and thus is critical for antigen binding like in the more typical tetrameric antibodies. The disclosure encompasses dimeric antibodies consisting of two heavy chains, or fragments thereof, that can bind to and/or inhibit the biological activity of C5.

The variable regions of the heavy and light chains typically exhibit the same general structure of relatively conserved framework regions (FR) joined by three complementarity determining regions or CDRs. The CDRs comprise hypervariable regions of an antibody that are responsible for antigen recognition and binding. The CDRs from the two chains of each pair are aligned and supported by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest. Chothia et al., 1987, *J. Mol. Biol.* 196:901-917; Chothia et al., 1989, *Nature* 342: 878-883.

CDRs constitute the major surface contact points for antigen binding. See, e.g., Chothia and Lesk, 1987, *J. Mol. Biol.* 196:901-917. Further, CDR3 of the light chain and, especially, CDR3 of the heavy chain may constitute the most important determinants in antigen binding within the light and heavy chain variable regions. See, e.g., Chothia and Lesk, 1987, supra; Desiderio et al., 2001, *J. Mol. Biol.* 310:603-615; Xu and Davis, 2000, *Immunity* 13:37-45; Desmyter et al., 2001, *J. Biol. Chem.* 276:26285-26290; and Muyldermans, 2001, *J. Biotechnol.* 74:277-302. In some antibodies, the heavy chain CDR3 appears to constitute the major area of contact between the antigen and the antibody. Desmyter et al., 2001, supra. In vitro selection schemes in which CDR3 alone is varied can be used to vary the binding properties of an antibody. Muyldermans, 2001, supra; Desiderio et al., 2001, supra.

Naturally occurring antibodies typically include a signal sequence, which directs the antibody into the cellular pathway for protein secretion and which is not present in the mature antibody. A polynucleotide encoding an antibody of the disclosure may encode a naturally occurring signal sequence or a heterologous signal sequence as described below.

In one embodiment, the anti-C5 antibody is a monoclonal antibody, with from one (1) to six (6) of the CDRs, as outlined herein. The antibodies of the disclosure can be of any type including IgM, IgG (including IgG1, IgG2, IgG3, IgG4), IgD, IgA, or IgE antibody. In some embodiments, the antibody is an IgG type antibody. In one embodiment, the antibody is an IgG2 type antibody.

In some embodiments, the antibody can comprise complete heavy and light chains, where the CDRs are all from the same species, e.g., human. Alternatively, for example in embodiments wherein the antibody contains less than six CDRs from the sequences outlined above, additional CDRs can be either from other species (e.g., murine CDRs), or can be different human CDRs than those depicted in the sequences. For example, human HC CDR3 and LC CDR3 regions from the appropriate sequences identified herein can be used, with HC CDR1, HC CDR2, LC CDR1 and LC CDR2 being optionally selected from alternate species, or different human antibody sequences, or combinations thereof. For example, the CDRs of the disclosure can replace the CDR regions of commercially relevant chimeric or humanized antibodies.

Specific embodiments can include scaffolds of the antibodies that comprise human sequences.

In some embodiments, however, the scaffold components can be a mixture from different species. As such, the antibody can be a chimeric antibody and/or a humanized antibody. In general, both chimeric antibodies and humanized antibodies can be antibodies that combine regions or amino acids from more than one species. For example, chimeric antibodies, in most embodiments, comprise variable region(s) from a mouse, rat, rabbit, or other suitable non-human animal, and the constant region(s) from a human. In other embodiments, chimeric antibodies comprise human FR sequences and non-human CDRs.

Humanized antibodies are antibodies that are originally derived from non-human antibodies, for example a mouse antibody. In various embodiments of a humanized anti-C5 antibody, the variable-domain framework regions or framework amino acids, which are derived from a non-human antibody, can be changed to amino acid identities found at corresponding positions in human antibodies. In some embodiments of a humanized antibody, the entire antibody, except the CDRs, can be encoded by a polynucleotide of human origin or can be identical to such an antibody except within its CDRs. In other embodiments, a humanized antibody may comprise specific amino acid positions whose identity has been changed to the identity of the same or similar position in a corresponding human antibody. The CDRs, some or all of which can be encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, *Nature* 321: 522-525, Verhoeyen et al., 1988, *Science* 239:1534-1536. Humanized antibodies can also be generated using mice with a genetically engineered immune system. Roque et al., 2004, *Biotechnol. Prog.* 20:639-654. In some embodiments, the CDRs can be human, and thus both humanized and chimeric antibodies, in this context, can include some non-human CDRs. In some cases, humanized antibodies can be generated that comprise the HC CDR3 and LC CDR3 regions, with one or more of the other CDR regions being of a different special origin.

In one embodiment, the C5 antibody can be a multispecific antibody, and notably a bispecific antibody, (e.g. diabodies). These are antibodies that bind to two (or more) different antigens, for example C5, and another antigen, or two different epitopes of C5. Diabodies can be manufactured in a variety of ways known in the art (Holliger and Winter, 1993, *Current Opinion Biotechnol.* 4:446-449), e.g., prepared chemically or from hybrid hybridomas.

In one embodiment, the anti-C5 antibody is a minibody. Minibodies are minimized antibody-like proteins comprising a scFv joined to a CH3 domain. Hu et al., 1996, *Cancer Res.* 56:3055-3061.

In one embodiment, the anti-C5 antibody is a domain antibody; see, for example U.S. Pat. No. 6,248,516. Domain antibodies (dAbs) are functional binding domains of antibodies, corresponding to the variable regions of either the heavy (VH) or light (VL) chains of human antibodies dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609, all incorporated entirely by reference.

In one embodiment, the anti-C5 antibody is an antibody fragment, that is a fragment of any of the antibodies outlined herein that retain binding specificity to C5. In various embodiments, the antibodies are a F(ab), F(ab'), F(ab')2, Fv, or a single chain Fv fragments. At a minimum, an antibody, as meant herein, comprises a polypeptide that can bind specifically to an antigen, wherein the polypeptide comprises all or part of a light and/or a heavy chain variable region.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, *Science* 242:423-426, Huston et al., 1988, *Proc. Natl. Acad. Sci. U.S.A.* 85:5879-5883), (viii) bispecific single chain Fv dimers (PCT/US92/09965) and (ix) diabodies or triabodies, multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). The antibody fragments can be modified. For example, the molecules can be stabilized by the incorporation of disulphide bridges linking the VH and VL domains (Reiter et al., 1996, *Nature Biotech.* 14:1239-1245).

In one embodiment, the C5 antibody is a traditional antibody, for example a human immunoglobulin. In this embodiment, as outlined above, specific structures comprise complete heavy and light chains depicted comprising the CDR regions. Additional embodiments utilize one or more of the CDRs of the disclosure, with the other CDRs, framework regions, J and D regions, constant regions, etc., coming from other human antibodies. For example, the CDRs of the disclosure can replace the CDRs of any number of human antibodies, particularly commercially relevant antibodies.

In one embodiment, the C5 antibody is an antibody fusion protein (e.g. an antibody conjugate). In this embodiment, the antibody is fused to a conjugation partner. The conjugate partner can be proteinaceous or non-proteinaceous; the latter generally being generated using functional groups on the antibody (see the discussion on covalent modifications of the antibodies) and on the conjugate partner. For example linkers are known in the art; for example, homo- or heterobifunctional linkers as are well known (see, Pierce Chemical Company catalog, technical section on cross-linkers, pages 155-200, incorporated herein by reference).

In one embodiment, the C5 antibody is an antibody analog. In some cases antibody analogs can be referred to as synthetic antibodies. For example, a variety of recent work utilizes either alternative protein scaffolds or artificial scaffolds with grafted CDRs. Such scaffolds include, but are not limited to, mutations introduced to stabilize the three-dimensional structure of the antibody as well as wholly synthetic scaffolds consisting for example of biocompatible polymers. See, for example, Korndorfer et al., 2003, *Proteins: Structure*, Function, and Bioinformatics, Volume 53, Issue 1:121-129. Roque et al., 2004, *Biotechnol. Prog.* 20:639-654. In addition, peptide antibody mimetics (PAMs) can be used, as well as work based on antibody mimetics utilizing fibronectin components as a scaffold.

VH and VL Variants

As outlined above, in some embodiments the disclosure provides antibodies comprising, or consisting of a heavy chain variable region comprising SEQ ID NO:2, 4, 6, 8, 10, and 12 and/or a light chain variable region of SEQ ID NO:1, 3, 5, 7, 9, and 11, respectively, or fragments thereof as defined above. Thus, in those embodiments, the antibody comprises not only at least one CDR or variant, but also at least part of a depicted framework sequence. In addition, the disclosure encompasses variants of such heavy chain variable sequences or light chain variable sequences.

A variant variable region, generally shares an amino acid homology, similarity, or identity of at least 80% with those of a parent variable region, such as those disclosed herein. In some embodiments, the variant and parent sequence homologies or identities are at least 75%, 80%, 85%, 90%, 91%, 92%, 93%, 94%, 95%, 96%, 97%, 98%, 99% and almost 100%. Nucleic acid sequence homology, similarity, or identity between the nucleotide sequences encoding individual variant VHs and VLs and the nucleic acid sequences depicted herein are at least 70% with those depicted herein, and more alternatively with increasing homologies or identities of at least 80%, 85%, 90%, 91%, 92%, 93%, 94%, 95%, 96%, 97%, 98%, 99% and almost 100%. In addition, a variant variable region can, in many embodiments, shares the biological function, including, but not limited to, at least 90%, 91%, 92%, 93%, 94%, 95%, 96%, 97%, 98% or 99% of the specificity and/or activity of the parent CDR. In some case, homology and/or identity is only measured outside the CDR sequences, which can be identical. In other cases, the homology and/or identity is measured throughout the entire sequence, including CDR sequences. In some embodiments, constant region variants may also be included.

In various cases, homology of amino acid sequences can reflect the percentage of identity or positives when optimally aligned as described above. In various cases, the % homology (% positive) or % identity can be calculated by dividing the number of aligned amino acids within a comparison window. A comparison window can be the entire length of one or the other compared polypeptides, if the two polypeptides are of unequal length. In other cases, the comparison window can be a portion of one of the polypeptides. In various cases the comparison window for measuring homology or identity of two polypeptide sequences is greater than about 40 aa (amino acids), 45 aa, 50 aa, 55 aa, 60 aa, 65 aa, 70 aa, 75 aa, 80 aa, 85 aa, 90 aa, 95 aa, 100 aa, 150 aa, or 200 aa, and/or less than about 200 aa, 150 aa, 100 aa, 95 aa, 90 aa, 85 aa, 80 aa, 75 aa, 70 aa, 65 aa, 60 aa, 55 aa, 50 aa, or 45 aa. In some embodiments, as in the case with various CDR sequences of the present disclosure, the comparison window may be less than 40 aa, for example between less than about 25 aa, 24 aa, 23 aa, 22 aa, 21 aa, 20 aa, 19 aa, 18 aa, 17 aa, 16 aa, 15 aa, 14 aa, 13 aa, 12 aa, 11 aa, 10 aa, 9 aa, 8 aa, 7 aa, 6 aa, 5 aa, or 4 aa, and greater than about 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, or 24 aa.

In various cases, the claimed amino acid sequences can have % identity or % homology (% positive) over a given comparison window, that is greater than about 70%, 75%, 80%, 85%, 90%, 91%, 92%, 93%, 94%, 95%, 96%, 97%, 98%, or 99% and/or less than about 100%, 99%, 98%, 97%, 96%, 95%, 94%, 93%, 92%, 91%, 90%, 85%, 80%, or 75%.

Covalent Modifications of Anti-C5 Antibodies

Covalent modifications of antibodies are included within the scope of this disclosure, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction can be performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues can be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antibodies to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (all incorporated entirely by reference) are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this disclosure.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Glycosylation

Another type of covalent modification of the antibodies included within the scope of this disclosure comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the disclosed antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody's amino acid sequence is altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) can be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting antibody can be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites can be prevented by the use of the compound tunicamycin as described by Duskin et al., 1982, *J. Biol. Chem.* 257:3105. Tunicamycin blocks the formation of protein-N-glycoside linkages.

PEGylation

Another type of covalent modification of the antibody comprises linking the antibody to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions can be made in various positions within the antibody to facilitate the addition of polymers such as PEG.

Labels

In some embodiments, the covalent modification of the antibodies of the disclosure comprises the addition of one or more labels.

The term "labelling group" means any detectable label. Examples of suitable labelling groups include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antibody via spacer arms of various lengths to reduce potential steric hindrance. Various methods for labelling proteins are known in the art and can be used in performing the present disclosure.

In general, labels fall into a variety of classes, depending on the assay in which they are to be detected: a) isotopic labels, which can be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and can be used in performing the present disclosure.

Specific labels include optical dyes, including, but not limited to, chromophores, phosphors and fluorophores, with the latter being specific in many instances. Fluorophores can be either "small molecule" fluores, or proteinaceous fluores.

A fluorescent label can be any molecule that can be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a Renilla, Ptilosarcus, or Aequorea species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), 13 galactosidase (Nolan et al., 1988, *Proc. Natl. Acad. Sci. U.S.A.* 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

Polynucleotides Encoding Anti-C5 Antibodies

In certain aspects, the disclosure provides nucleic acid molecules encoding the antibodies described herein. In some cases the disclosed nucleic acids code for antibodies, variable regions, or CDRs described herein. Nucleic acids include both DNA and RNA molecules. Nucleic acids can be either natural, non-natural nucleic acids, nucleic acid analogs, or synthetic nucleic acids. Nucleic acids of the present disclosure are typically polynucleic acids; that is, polymers of individual nucleotides that are covalently joined by phosphodiester bonds. In various cases the nucleotide sequences can be single-stranded, double stranded, or a combination thereof. The nucleotide sequences can further comprise other non-nucleic acid molecules such as amino acids, and other monomers.

In many embodiments, the coding sequence may be an isolated nucleic acid molecule. The isolated nucleic acid molecule is identified and separated from at least one component with which it is ordinarily associated in the natural source. In some cases a component can be a nucleotide sequence, protein, or non-proteinaceous molecule. An isolated anti-C5 antibody-encoding nucleic acid molecule is other than in the form or setting in which it is found in nature. Isolated anti-C5 antibody-encoding nucleic acid molecules therefore are distinguished from the encoding nucleic acid molecule(s) as they exist in natural cells. However, an isolated anti-C5 antibody-encoding nucleic acid molecule includes anti-C5 antibody-encoding nucleic acid molecules contained in cells that ordinarily express anti-C5 antibody where, for example, the nucleic acid molecule is in a chromosomal location different from that of natural cells. Isolated nucleic acid molecules therefore are distinguished from the nucleic acid molecule as it exists in an organism. However, in some cases an isolated nucleic acid molecule can be a nucleic acid contained within a cell, for example, wherein the isolated nucleic acid molecule is introduced into a cell and resides in either an extrachromosomal location or in a chromosomal location different from its native location.

Depending on its use, the nucleic acid can be double stranded, single stranded, or contain portions of both double stranded or single stranded sequence. As will be appreciated by those in the art, the depiction of a single strand (sometimes referred to as the "Watson" strand) also defines the sequence of the other strand (sometimes referred to as the "Crick" strand). A recombinant nucleic can be a nucleic acid, originally formed in vitro, in general, by the manipulation of nucleic acid by endonucleases, in a form not normally found in nature. Thus an isolated antibody can be encoded by a nucleic acid, in a linear form, or an expression vector formed in vitro by ligating DNA molecules that are not normally joined, are both considered recombinant for the purposes of this disclosure. It is understood that once a recombinant nucleic acid, with all necessary control elements, is made and reintroduced into a host cell or organism, it can replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the disclosure.

In some embodiments, the recombinant nucleic acid may comprise one or more control elements or control sequences. Control element and control sequence refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. As used herein, an operably linked sequence, is a nucleic acid sequence in a functional relationship with another nucleic acid sequence. For example, nucleic acid coding sequences can be operably linked to nucleic acid control sequences. For example, DNA for a presequence or secretory leader can be operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. In most embodiments, an operably linked sequence is a DNA sequence covalently linked to, for example, a secretory leader sequence. However, as described above, some control sequences can be active as RNA sequence. In many embodiments, enhancer sequences are not required to be adjacent to a coding sequence, rather the two sequences may be separated by one or more nucleic acids.

In various cases, the nucleic acids of the disclosed nucleotide sequences can include nucleotides that are metabolized in a manner similar to naturally occurring nucleotides. Also included are nucleic-acid-like structures with synthetic backbone analogues including, without limitation, phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs) (see, e.g.: "Oligonucleotides and Analogues, a Practical Approach," edited by F. Eckstein, IRL Press at Oxford University Press (1991); "Antisense Strategies," Annals of the New York Academy of Sciences, Volume 600, Eds. Baserga and Denhardt (NYAS 1992); Milligan (1993) J. Med. Chem. 36:1923-1937; and "Antisense Research and Applications" (1993, CRC Press)). PNAs contain non-ionic backbones, such as N-(2-aminoethyl) glycine units. Phosphorothioate linkages are described in: WO 97/03211; WO 96/39154; and Mata (1997) Toxicol. Appl. Pharmacol. 144: 189-197. Other synthetic backbones encompassed by this term include methyl-phosphonate linkages or alternating methyl-phosphonate and phosphodiester linkages (Strauss-Soukup (1997) Biochemistry 36: 8692-8698), and benzyl-phosphonate linkages (Samstag (1996) Antisense Nucleic Acid Drug Dev 6: 153-156).

As will be appreciated by those in the art, due to the degeneracy of the genetic code, an extremely large number of nucleic acids can be made, all of which encode the CDRs (and heavy and light chains or other components of the antibody) of the present disclosure. Thus, having identified a particular amino acid sequence, those skilled in the art could make any number of different nucleic acids, by simply modifying the sequence of one or more codons in a way which does not change the amino acid sequence of the encoded protein.

In various cases, nucleotide sequences encoding the polypeptide sequences of SEQ ID NOS:1-48 are included. These nucleotide coding sequences can be translated into a polypeptide having an amino acid sequence identical to the disclosed polypeptide sequence. In many cases, nucleotides coding for identical polypeptides, may not have identical nucleotide sequences. The disclosed coding sequences can further comprise untranslated sequences, for example polyadenylation sequences. The inventive coding sequences can also comprise intron or intervening, non-translated, sequence that are spliced out of a transcribed mRNA prior to translation. In various cases the transcribed mRNA can be capped with a terminal 7-methylguanosine. In some embodiments, the coding sequences will include coding sequences for amino acids that do not appear in the final antibody, for example sequences required for export of the antibody.

The nucleotide coding sequences can be aligned by BLASTn, as described above. In various cases the homology (or identities in BLASTn) of these aligned nucleotide sequences can be greater than about 40%, 45%, 50%, 55%, 60%, 65%, 70%, 75%, 80%, 85%, 90%, or 95% and/or less than about 100%, 95%, 90%, 85%, 80%, 75%, 70%, 65%, 60%, 55%, 50%, or 45%. In various cases, the homologous aligned sequences can be less than about 700 nt, 600 nt, 500 nt, 400 nt, 300 nt, 200 nt, 100 nt, 90 nt, 80 nt, 70 nt, 60 nt, 50 nt or 40 nt, and/or more than about 50 nt, 60 nt, 70 nt, 80 nt, 90 nt, 100 nt, 200 nt, 300 nt, 400 nt, 500 nt, or 600 nt.

In various cases, the coding sequence directs transcription of a ribonucleic acid sequence that can be translated into amino acid sequence according to the standard genetic code. In various cases, the code can include variations to the canonical code. In some variations, the coding sequence can include introns, or intervening sequences that do not code for amino acids, but can be transcribed and later removed before the ribonucleic acid is translated into a polypeptide.

Methods of Producing Antibodies

The present disclosure also provides expression systems and constructs in the form of plasmids, expression vectors, transcription or expression cassettes which comprise at least one polynucleotide as above. In addition, the disclosure provides host cells comprising such expression systems or constructs.

Typically, expression vectors used in any of the host cells will contain sequences for plasmid maintenance and for cloning and expression of exogenous nucleotide sequences. Such sequences, collectively referred to as flanking sequences in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the C5 antibody coding sequence; the oligonucleotide sequence can encode a polyHis tag (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the C5 antibody from the host cell. Affinity purification can be accomplished, for example, by column chromatography using antibodies against the tag as an affinity matrix. Optionally, the tag can subsequently be removed from the purified anti-C5 antibody by various means such as using certain peptidases for cleavage.

Flanking sequences can be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence can be any prokaryotic or eukaryotic organism, any vertebrate or invertebrate organism, or any plant, provided that the flanking sequence is functional in, and can be activated by, the host cell machinery.

Flanking sequences useful in the vectors of this disclosure can be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence can be known. Here, the flanking sequence can be synthesized using the methods described herein for nucleic acid synthesis or cloning.

Whether all or only a portion of the flanking sequence is known, it can be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence can be isolated from a larger piece of DNA that may contain, for example, a coding sequence or even another gene or genes. Isolation can be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one can be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes can be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to a C5 polypeptide or C5 epitope. As a result, increased quantities of a polypeptide such as a anti-C5 antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the disclosure will typically contain a promoter that is recognized by the host organism and operably linked to the molecule encoding the C5 antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising a C5 antibody of the disclosure by removing the promoter from the source DNA by restriction enzyme digestion and inserting the desired promoter sequence into the vector.

In some embodiments, yeast cells may be used to produce the presently disclosed anti-C5 antibodies. Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and or Simian Virus 40 (SV40). Other suitable mammalian promoters include heterologous mammalian promoters, for example, heat-shock promoters and the actin promoter.

Additional promoters which can be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence can be inserted into the vector to increase transcription of DNA encoding light chain or heavy chain comprising a C5 antibody of the disclosure by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer can be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

Expression vectors, for expressing the presently claimed antibodies of the disclosure can be constructed from a starting vector such as a commercially available vector. Such vectors may or may not contain all of the desired flanking sequences. Where one or more of the flanking sequences described herein are not already present in the vector, they can be individually obtained and ligated into the vector. Methods used for obtaining each of the flanking sequences are well known to one skilled in the art.

After the vector has been constructed and a nucleic acid molecule encoding a light chain, a heavy chain, or a light chain and a heavy chain comprising an anti-C5 antibody coding sequence has been inserted into the proper site of the vector, the completed vector can be inserted into a suitable host cell for amplification and/or polypeptide expression. The transformation of an expression vector for an anti-C5 antibody into a selected host cell can be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an anti-C5 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell can be eukaryotic or prokaryotic.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and constitutively produce antibodies with C5 binding properties. In another embodiment, a cell line from the B cell lineage that does not make its own antibody but has a capacity to make and secrete a heterologous antibody can be selected.

Use of Anti-C5 Antibodies for Diagnostic and Therapeutic Purposes

Antibodies of the disclosure are useful for detecting C5 and/or C5b in biological samples and identification of cells or tissues that produce C5 protein. In some embodiments, the anti-C5 antibodies of the disclosure can be used in diagnostic assays, e.g., binding assays to detect and/or quantify C5 expressed in a tissue or cell or C5b in a serum or tissue, or on a cell.

In some embodiments, the antibodies of the disclosure that specifically bind to C5 can be used in treatment of Complement or C5-mediated diseases in a patient in need thereof. In addition, the anti-C5 antibody of the disclosure can be used to inhibit C5 from forming a complex with other complement proteins, thereby modulating the biological activity of C5 in a cell or tissue. Antibodies that bind to C5 thus can modulate and/or block interaction with other binding compounds and as such may have therapeutic use in ameliorating Complement and C5 mediated diseases.

In some embodiments, the binding of C5 by anti-C5 antibodies may result in disruption of the C5-mediated complement cascade.

Diagnostic Methods

The antibodies of the disclosure can be used for diagnostic purposes to detect, diagnose, or monitor diseases and/or conditions associated with complement or C5. The disclosure provides for the detection of the presence of C5 in a sample using classical immunohistological methods known to those of skill in the art (e.g., Tijssen, 1993, *Practice and Theory of Enzyme Immunoassays*, vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of C5 can be performed in vivo or in vitro.

Diagnostic applications provided herein include use of the antibodies to detect expression of C5. Examples of methods useful in the detection of the presence of C5 include immunoassays, such as the enzyme linked immunosorbent assay (ELISA) and the radioimmunoassay (RIA).

For diagnostic applications, the antibody typically can be labeled with a detectable labeling group. Suitable labeling groups include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antibody via spacer arms of various lengths to reduce potential steric hindrance. Various methods for labelling proteins are known in the art and can be used in performing the present disclosure.

One aspect of the disclosure provides for identifying a cell or cells that express C5. In a specific embodiment, the antibody is labeled with a labeling group and the binding of the labeled antibody to C5 is detected. In a further specific embodiment, the binding of the antibody to C5 can be detected in vivo. In a further specific embodiment, the antibody/C5 complex is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology New York*: John Wiley & Sons.

Another aspect of the disclosure provides for detecting the presence of a test molecule that competes for binding to C5 with the anti-C5 antibodies of the disclosure. An example of one such assay would involve detecting the amount of free antibody in a solution containing an amount of C5 in the presence or absence of the test molecule. An increase in the amount of free antibody (i.e., the antibody not bound to C5) would indicate that the test molecule is capable of competing for C5 binding with the anti-C5 antibody. In one embodiment, the antibody is labeled with a labeling group. Alternatively, the test molecule is labeled and the amount of free test molecule is monitored in the presence and absence of an antibody.

Indications

The complement system has been implicated in contributing to several acute and chronic conditions, including atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration.

Macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. One group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The presently disclosed anti-C5 antibodies can be used in combination with one or more cytokines, lymphokines, hematopoietic factor(s), and/or an anti-inflammatory agent. Treatment of the diseases and disorders recited herein can include the use of first line drugs for control of pain and inflammation in combination (pretreatment, post-treatment, or concurrent treatment) with treatment with one or more of the anti-C5 antibodies provided herein. In some cases the drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the present disclosure is directed to the use of an antibody and any of one or more NSAIDs for the treatment of the diseases and disorders recited herein. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In another specific embodiment, the present disclosure is directed to the use of an antibody in combination (pretreatment, post-treatment, or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In an additional specific embodiment, the present disclosure is directed to the use of an antibody in combination (pretreatment, post-treatment, or concurrent treatment) with any of one or more propionic acid derivatives, prodrug esters or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the present disclosure is directed to the use of an antibody in combination (pretreatment, post-treatment, or concurrent treatment) with any of one or more acetic acid derivatives, prodrug esters or pharmaceutically acceptable salts thereof. The acetic acid derivatives, prodrug esters, and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the present disclosure is directed to the use of an antibody in combination (pretreatment, post-treatment, or concurrent treatment) with any of one or more carboxylic acid derivatives, prodrug esters or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the present disclosure is directed to the use of an antibody in combination (pretreatment, post-treatment, or concurrent treatment) with any of one or more butyric acid derivatives, prodrug esters or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In still another specific embodiment, the present disclosure is directed to the use of an antibody in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which can be used comprise: difenamizole and epirizole. Structurally related pyrazoles having similar analgesic and anti-inflammatory properties are also intended to be encompassed by this group.

In an additional specific embodiment, the present disclosure is directed to the use of an antibody in combination (pretreatment, post-treatment or, concurrent treatment) with any of one or more pyrazolones, prodrug esters, or pharmaceutically acceptable salts thereof. The pyrazolones, prodrug esters and pharmaceutically acceptable salts thereof which can be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more of the following NSAIDs: $\epsilon$-acetamidocaproic acid, S-adenosyl-methionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the present disclosure is directed to the use of an antibody in combination (pretreatment, post-treatment or concurrent treatment) with any of one or more corticosteroids, prodrug esters or pharmaceutically acceptable salts thereof for the treatment of the diseases and disorders recited herein, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydro-cortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclo-phosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more COX2 inhibitors, prodrug esters or pharmaceutically acceptable salts thereof for the treatment of the diseases and disorders recited herein, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group. Examples of COX-2 selective inhibitors include but not limited to etoricoxib, valdecoxib, celecoxib, licofelone, lumiracoxib, rofecoxib, and the like.

In still another specific embodiment, the present disclosure is directed to the use of an antibody in combination (pretreatment, post-treatment, or concurrent treatment) with any of one or more antimicrobials, prodrug esters or pharmaceutically acceptable salts thereof for the treatment of the diseases and disorders recited herein, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazine, sulfisoxazole and co-trimoxazole (trimethoprim/sulfamethoxazole). The lincosamides include, but are not limited to clindamycin and lincomycin. The polymyxins (polypeptides) include, but are not limited to polymyxin B and colistin.

Methods of Treatment: Pharmaceutical Formulations, Routes of Administration

Compositions are disclosed comprising a therapeutically effective amount of one or a plurality of the antibodies of the disclosure together with a pharmaceutically acceptable diluent, carrier, solubilizer, emulsifier, preservative, and/or adjuvant. In addition, the disclosure provides methods of treating a patient by administering such pharmaceutical composition. A patient can be either a human subject or an animal subject.

Pharmaceutical compositions comprising one or more anti-C5 antibodies can be used to reduce C5 activity. Pharmaceutical compositions comprising one or more antibodies can be used in treating the consequences, symptoms, and/or the pathology associated with C5 activity. In various embodiments, pharmaceutical compositions comprising one or more antibodies can be used in methods of inhibiting the complement pathway. Pharmaceutical compositions comprising one or more antibodies can be used in methods of treating the consequences, symptoms, and/or the pathology associated with C5 activity. Pharmaceutical compositions comprising one or more antibodies can be used in methods of inhibiting MAC production. Pharmaceutical compositions comprising one or more antibodies can be used in methods of inhibiting Macular Degeneration.

Various acceptable formulation materials are nontoxic to recipients at the dosages and concentrations employed. In specific embodiments, pharmaceutical compositions comprising a therapeutically effective amount of anti-C5 antibodies are provided.

In certain embodiments, acceptable formulation materials are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, sodium or potassium chloride, mannitol sorbitol); delivery vehicles; diluents; excipients and/or pharmaceutical adjuvants. See, REMINGTON'S PHARMACEUTICAL SCIENCES, 18$^{th}$ Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the disclosure. In certain embodiments, the primary vehicle or carrier in a pharmaceutical composition can be either aqueous or non-aqueous in nature. For example, a suitable vehicle or carrier can be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the disclosure, C5 antibody compositions can be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the C5 antibody product can be formulated as a lyophilizate using appropriate excipients such as sucrose.

The pharmaceutical compositions of the disclosure can be selected for parenteral delivery. Alternatively, the compositions can be selected for inhalation or for delivery through the digestive tract, such as orally. Preparation of such pharmaceutically acceptable compositions is within the skill of the art.

The formulation components can be present in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this disclosure can be provided in the form of a pyrogen-free, parenterally acceptable aqueous solution comprising the desired C5 antibody in a pharmaceutically acceptable vehicle. A particularly suitable vehicle for parenteral injection is sterile distilled water in which the C5 antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices can be used to introduce the desired antibody.

Pharmaceutical compositions of the disclosure can be formulated for inhalation. In these embodiments, C5 antibodies are advantageously formulated as a dry, inhalable powder. In specific embodiments, C5 antibody inhalation solutions may also be formulated with a propellant for aerosol delivery. In certain embodiments, solutions can be nebulized. Pulmonary administration and formulation methods therefore are further described in International Patent Application No. PCT/US94/001875, which is incorporated by reference and describes pulmonary delivery of chemically modified proteins. It is also contemplated that formulations can be administered orally. C5 antibodies that are administered in this fashion can be formulated with or without carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized Additional agents can be included to facilitate absorption of the C5 antibody. Diluents, flavorings, low melting point waxes, vegetable oils, lubricants, suspending agents, tablet disintegrating agents, and binders may also be employed.

A pharmaceutical composition of the disclosure is provided to comprise an effective quantity of one or a plurality of C5 antibodies in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving C5 antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules.

Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method can be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, crystal, or as a dehydrated or lyophilized powder. Such formulations can be stored either in a ready-to-use form or in a form (e.g., lyophilized) that is reconstituted prior to administration. The disclosure also provides kits for producing a single-dose administration unit. The kits of the disclosure may each contain both a first container having a dried protein and a second container having an aqueous formulation. In certain embodiments of this disclosure, kits containing single and multi-chambered pre-filled syringes (e.g., liquid syringes and lyosyringes) are provided.

The therapeutically effective amount of a C5 antibody-containing pharmaceutical composition to be employed will depend, for example, upon the therapeutic context and objectives. One skilled in the art will appreciate that the appropriate dosage levels for treatment will vary depending, in part, upon the molecule delivered, the indication for which the C5 antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 0.1 µg/kg up to about 30 µg/kg, optionally from 1 µg/kg up to about 30 mg/kg or from 10 µg/kg up to about 5 mg/kg.

Dosing frequency will depend upon the pharmacokinetic parameters of the particular C5 antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data. In certain embodiments, the antibodies of the disclosure can be administered to patients throughout an extended time period. Chronic administration of an antibody of the disclosure minimizes the adverse immune or allergic response commonly associated with antibodies that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intra-parenchymal), intracerebroventricular, intramuscular, intra-ocular, intravitreal, sub-retinal, intraarterial, intraportal, or intralesional routes; by sustained release systems or by implantation devices. In certain embodiments, the compositions can be administered by bolus injection or continuously by infusion, or by implantation device.

The composition also can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. For ocular implants, the implant can be implanted via intra-ocular injection, intravitreal injection, sub-retinal injection, suprachoroidal injection, retrobulbar injection or injection into sub-Tenon space.

It also can be desirable to use C5 antibody pharmaceutical compositions according to the disclosure ex vivo. In such instances, cells, tissues or organs that have been removed from the patient are exposed to C5 antibody pharmaceutical compositions after which the cells, tissues and/or organs are subsequently implanted back into the patient.

In particular, C5 antibodies can be delivered by implanting certain cells that have been genetically engineered, using methods such as those described herein, to express and secrete the C5 antibody. In certain embodiments, such cells can be animal or human cells, and can be autologous, heterologous, or xenogeneic. In certain embodiments, the cells can be immortalized. In other embodiments, in order to decrease the chance of an immunological response, the cells can be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

All references cited within the body of the instant specification are hereby expressly incorporated by reference in their entirety.

EXAMPLES

The following examples, including the experiments conducted and the results achieved, are provided for illustrative purposes only and are not to be construed as limiting the disclosure.

Example 1

Immunization and Hybridoma Creation

For generation of hybridomas and monoclonal antibodies, immunization and screening were conducted essentially as described in Antibodies, *A laboratory Mannual, Cold Spring Harbor Laboratory*. The procedure specific to the generation of anti-C5 monoclonal antibodies as described in this application is briefly described as follows. B10.D2-Hc$^O$H2$^d$H2-T18$^c$/O2SnJ mice deficient in complement C5 (Jackson Labs®, Bar Harbor maine), were immunized by foot pad injection using 75 μg of human C5 (Quidel® cat#A403) in Complete Freunds adjuvant, followed by sequential secondary boosts by intraperitoneal (I.P.) administration using 75 μg C5 protein with Incomplete Freund's adjuvant on day 28. ELISA screen for serum titers for reactivity against C5 protein were conducted 9-10 days post-secondary boost. For the initial set of fusions mice showing favorable titers were immunized with fusion boosts (75 μg C5 in pBS, I.P.) on day 82, 83 and 84 with spleen fusion into SP2/0 mouse myeloma using standard techniques on day 85. A second cohort of mice was further immunized on day 68 and 175 followed by fusion boosts day 195, 196 and 197 with fusion on day 198. All fusion wells were screen for reactivity against C5 protein by ELISA 18 days post fusion and positive hybridomas subcloned using standard techniques allowing derivation of monoclonal antibodies.

Example 2

Hybridoma Culture

The hybridomas were maintained in DMEM containing 15% Fetal Clone II, OPI, HAT, non-essential amino acids and recombinant mouse IL-6. Hybridoma supernatants were screened by enzyme-linked immunosorbent assay (ELISA) to detect antihuman C5 antibodies. Positive cultures for C5 were expanded in DMEM containing 15% Fetal Clone II, OPI and non-essential amino acids, and subcloned twice by limiting dilution. The subcloned hybridomas were isotyped with SBA Clonotyping System/HRP (SouthernBiotech) according to the manufacturer's protocol.

Example 3

Cloning and Sequence Determination of Monoclonal Variable Heavy and Light Chain Domains Variable light (VL) and heavy (VH) chains domains were cloned following the de novo RT-PCR amplification. Briefly, total RNA was isolated from selected subcloned hybridoma cell lines using a total RNA isolation kit (Qiagen®). cDNA synthesis was performed using the First Strand cDNA Synthesis Kit (Invitrogen®). The forward primers were specific for the N-terminal amino acid sequence of the VL and VH region, and the LC and HC reverse primers were designed to anneal to a region in the constant light (CL) and constant heavy domain 1 (CH1). The primers used for do novo cloning is listed below. Amplified VL or VH fragments were isolated and subcloned into pCR®II-TOP vector (Invitrogen®, Life Technologies®) and sequenced using standard methods.

TABLE 4

| | Primers |
|---|---|
| VH Forward Primers SEQ ID NO: 49 | MuIgVH5' GGGAATTCATGRASTTSKGGYTMARCT KGRTTTGGGAATTCATGRAATGSASCTGGGTYWTYC TCTTACTAGTCGACATGAAGWTGTGGBTRAACTGGR TACTAGTCGACATGGRATGGASCKKIRTCTTTMTCT ACTAGTCGACATGAACTTYGGGYTSAGMTTGRTTTA CTAGTCGACATGTACTTGGGACTGAGCTGTGTATAC TAGTCGACATGAGAGTGCTGATTCTTTTGTGACTAG TCGACATGGATTTTGGGCTGATTTTTTTTATTG |
| VH Reverse Primers SEQ ID NO: 50 | MuIgGVH3'-CCCAAGCTTCCAGGGRCCARKGGATA RACIGRTGG |
| VL Forward primers SEQ ID NO: 51 | MuIgKVL5' GGGAATTCATGRAGWCACAKWCYCAG GTCTTTACTAGTCGACATGAGIMMKTCIMTTCAITT CYTGGGACTAGTCGACATGAKGTHCYCIGCTCAGYT YCTIRGACTAGTCGACATGGTRTCCWCASCTCAGTT CCTTGACTAGTCGACATGTATATATGTTTGTTGTCT ATTTCTACTAGTCGACATGAAGTTGCCTGTTAGGCT GTTGGTGCTACTAGTCGACATGGATTTWCARGTGCA GATTWTCAGCTTACTAGTCGACATGGTYCTYATVTC CTTGCTGTTCTGGACTAGTCGACATGGTYCTYATVT TRCTGCTGCTATGG |
| VL Reverse Primers SEQ ID NO: 52 | MuIgKVL3' CCCAAGCTTACTGGATGGTGGGAAGA TGGA |

PCR was performed as follows:
cDNA 5 μL
10× PCR buffer 5 μL
dNTP 1 μL
primer mix 2.5 μL
Polymerase 1 μL
dH2O 35.5 μL
Total volume, 50 μL

TABLE 5

| PCR Conditions | | |
|---|---|---|
| Step | Temp (° C.) | Time (min) |
| 1 | 95 | 5:00 |
| 2 | 95 | 0:30 |
| 3 | 58 | 0:30 |
| 4 | 72 | 3:00 |
| 5 | Return to Step 2, repeat 34 times | |
| 6 | 72 | 5:00 |
| 7 | 4 | storage |

Example 4

Anti-C5 Inhibitory Activity Screen (CH50 Hemolytic Assay)

Sheep red blood cells (RBC) (innovative research IC100-0210) were primed by incubating anti-RBC stroma antibody (Sigma Aldrich, Cat. No. 58014) for 1 hour at 37° C. followed by washing and resuspension in GVB++ buffer at a concentration of $5 \times 10^8$/mL and stored at 4° C. until use. For analysis of hemolytic activity, RBCs were diluted to a final concentration of $4.1 \times 10^7$/ml in the presence of human serum in GVB++ buffer followed by incubation for 1 hour at 37° C. The level of hemolytic activity was determined by pelleting unlysised RBC and cellular debris at 10,000×g for 10 minutes at 4° C. and measuring levels of released hemoglobin in the supernatant by monitoring the absorbance at 541 nm. In studies examining functional activity of antibodies, serum and antibodies were incubated for 20 minutes at 4° C. prior to addition to red blood cells. For testing activity in hybridoma cell culture supernatants, supernatants were incubated with 3% NHS in GVB buffer at 1:1 ratio for 60 minutes at 4° C. prior to the addition of primed RBC. Controls included serum alone (positive control), dH$_2$O (100% lysis), and Serum+EDTA 10 mM (negative control) For analysis of the alternative pathway GVB+ 10 mM EGTA (Boston Bioproducts IBB-310) and C1Q deficient human serum (Quidel, A509) was used. In some assays unprimed rabbit red blood cells (1×10$^7$) are substituted for sheep red blood cells and the assay is run in the presence of GVB buffer containing 0.5 mM EGTA (Boston Bioproducts IBB-310).

FIG. 3 is a graphical representation of the results of the hemolytic assay for a selected number of clones screened. The black line between clones 5B201 and 5D7-5 represents results from the commercially purchase mouse monoclonal antibody A239 (Quidel A239). Clones to the left of this line represents antibodies that showed higher/better inhibition of complement activation (which results in lysis of cells). One subclone of particular interest was 10C9 (and progeny, with the nomenclature of 10C9-X, with X representing a different subclone number from the parent).

Example 5

Anti-C5 Inhibitory Activity Screen (IgM ELISA Assay)

96-well EIA plates (Costar #3590) were coated with 2 µg/ml human IgM in coating buffer pH 9.5. (BD-biosciences 51-2713KC) overnight at 4° C. Plates were washed using wash buffer (BD-biosciences 51-9003739). Serum diluted to 2% in GVB (BD-biosciences 51-2713KC) and was combined with varying concentration of hybridoma supernatant or purified IgGs and incubated for 20 minutes at 4° C. After the incubation period 100 ul of the serum/antibody mixture is added to the washed IgM coated plates and incubated for 1 hr at 37° C. After the incubation period plates were washed three times with wash buffer and then incubated with anti-C5b-9 mouse monoclonal antibody (Quidel A239) at a 1:10.000 dilution in assay diluent (BD-biosciences 51-2641KC) for 30 minutes at room temperature. After incubation plates were washed three times and then probed with goat anti-mouse HRP conjugate diluted 1:3000 in assay diluent. Plates were incubated for 30 minutes and the washed three times in wash buffer and the signal detected by the addition of substrate (BD-biosciences 51-2606KZ and BD-biosciences 51-2607KZ) followed by incubation at room temperature for 10 minutes prior to addition of stop solution (BD-biosciences 51-2608KZ). Level of complement activation was then determined by read the absorption at 450 nm.

Figure 5A:
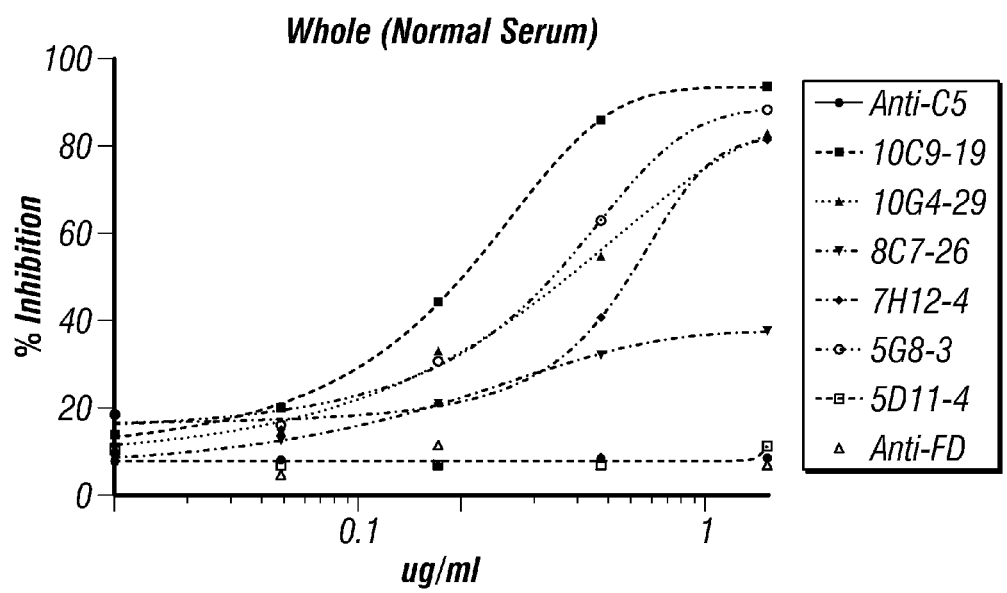
FIGS. 5A, 5B, and 5C show percent inhibition of MAC by anti-C5 antibody sub-clones.
Figure 5B:
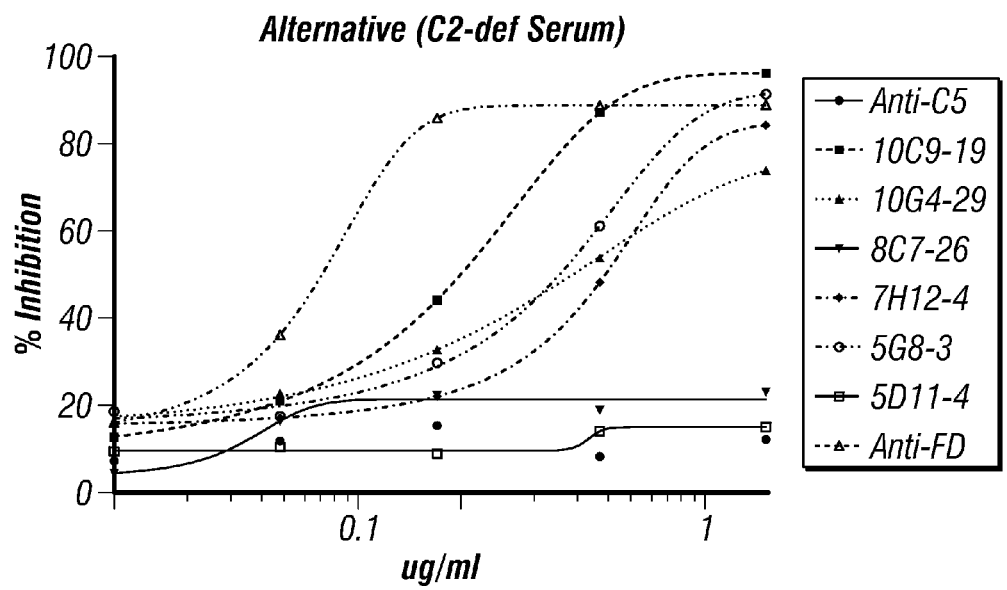
Figure 5C:
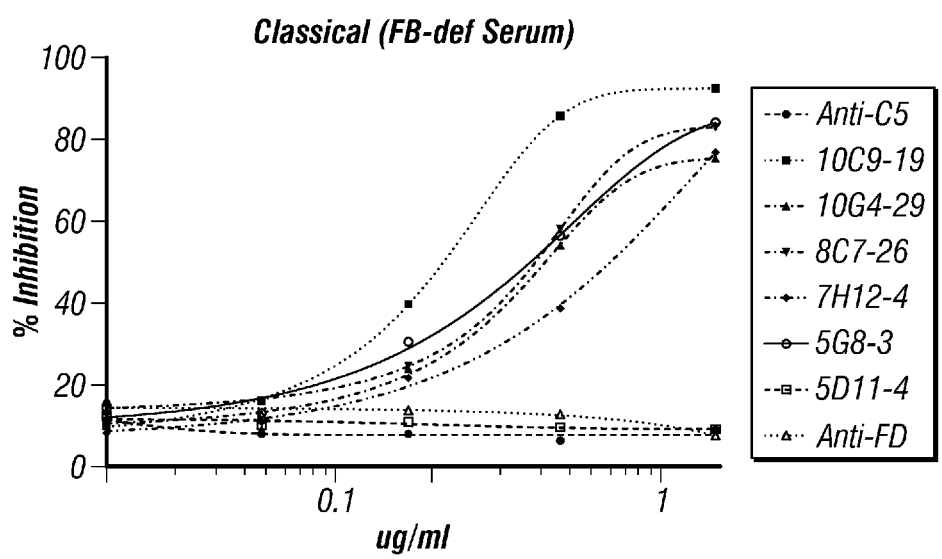

FIGS. 5A, 5B, and 5C shows the results of the IgM ELISA using whole serum, in which all complement pathways are active; using C2 deficient serum, where only the alternative pathway is active; and using Factor B deficient serum where the classical and lectin pathways are active. The A239 antibody (Quidel A239) against C5 (labelled Anti-C5 in FIGS. 5A-5C) served as a negative control. An anti-Factor D antibody (labelled Anti-FD in FIGS. 5A-5C) served as a positive control comparator in the alternative pathway (FIG. 5B). Overall, the 10C9-19 antibody performed equally well under all three conditions serum conditions.

Example 6

Figure 7:
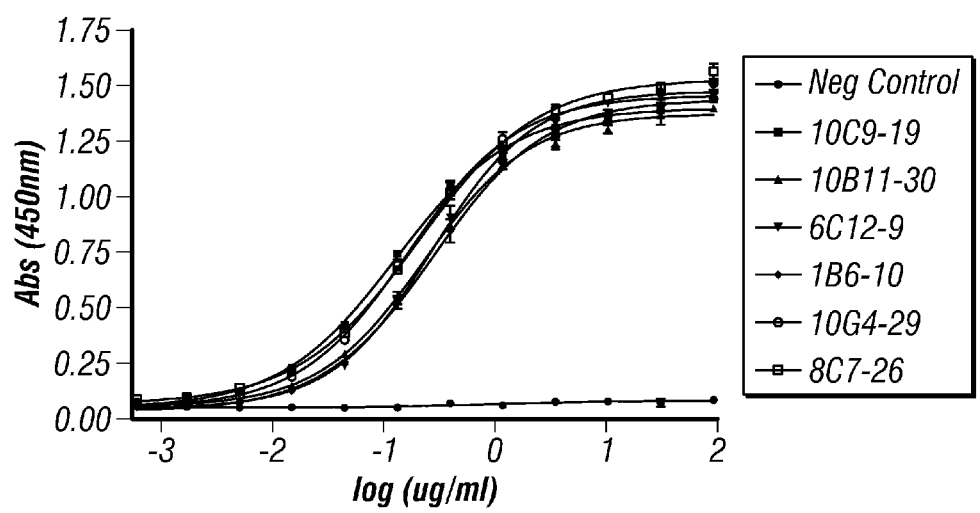
FIG. 7 shows dose dependent interaction of monoclonal antibodies with C5 directly coated on to an ELISA plates.

Anti-C5 ELISA 96-well EIA plates (Costar #3590) are coated with 1 µg/ml Human C5 in coating buffer pH 9.5. (BD-biosciences 51-2713KC) overnight at 4° C. Following day plates were washed Plates are washed using wash buffer (BD-biosciences 51-9003739), and then blocked for 30 minutes using Assay Diluent (BD-biosciences 51-2641KC). Purified monoclonal antibodies or hybridoma supernatants were then diluted in to assay diluent and added to wells previously coated with C5 and incubated at room temperature for 60 minutes. Plates were washed 3 times and the level of bound monoclonal detected using at mouse HPR conjugated secondary and substrate. Level of bound antibody was determined by measuring absorbance at 450 nM. FIG. 7 is a graphical representation of the binding of C5 using selected monoclonal antibodies/hybridoma supernatants.

Example 7

Detection of Insoluble C5b-9 Assay 96-well EIA plates (Costar #3590) are coated with 2n/ml Human IgM IgM (V) in coating buffer pH 9.5. (BD-biosciences 51-2713KC) overnight at 4° C. Plates are washed using wash buffer (BD-biosciences 51-9003739). Normal Human Serum was diluted to 2% in GVB (BD-biosciences 51-2713KC) and 100 µl of the Serum/GVB mixture was added to the washed IgM coated plates and incubated for 1 hr at 37° C. After the incubation period plates are washed three times with wash buffer and then incubated with anti-C5 monoclonal antibodies diluted in to assay diluent to the concentrations as indicated in the figure. After incubation plates were washed three times and then probed for 30 minutes with anti-mouse HRP conjugate secondary diluted 1:3000 in assay diluent followed by washing three times in wash buffer. Bound antibody was then detected by the addition of substrate (BD-biosciences 51-2606KZ and BD-biosciences 51-2607KZ) followed by incubation at room temperature for 10 minutes prior to addition of stop solution (BD-biosciences 51-2608KZ). Level of complement activation is then determined by read the absorption at 450 nm.

Figure 10:
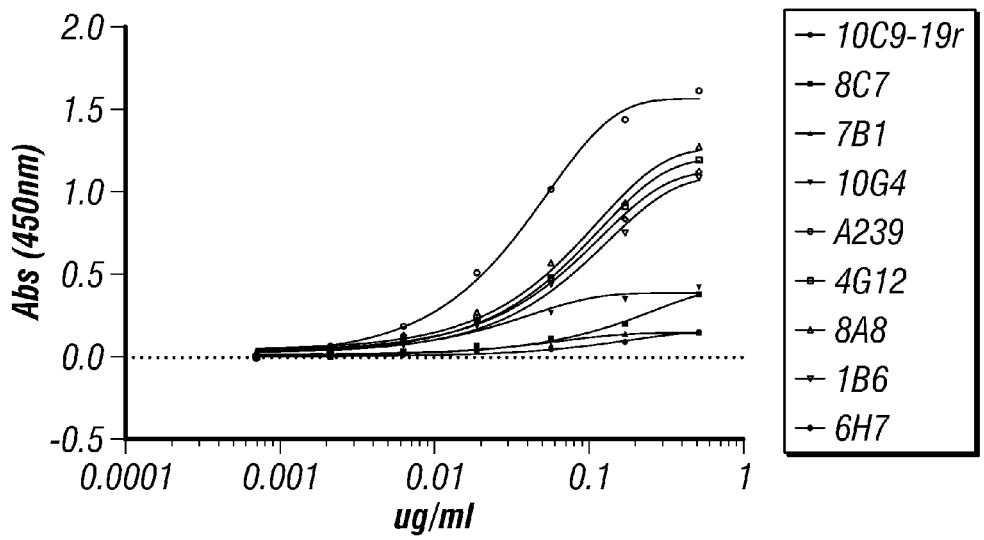
FIG. 10 shows ability to recognize C5 with in the C5b-9 complex when deposited into the bottom of ELISA plates after complement activation with IgM.

FIG. 10 shows a graphical representation of the results. Of the monoclonal antibodies screened, 10C9-19r (r is used to designate that the antibody that was used is a recombinant version of the 10C9-19 clone) does not bind to insoluble C5b9. This is consistent with the hypothesis that this antibody does not recognize or bind C5 after it has been incorporate to MAC.

Example 8

Detection of Soluble C5b-9

Amine reactive tips (AR2G) (ForteBio®, 18-5092) were used for the immobilization of antibodies in the OCTET RED 96 (ForteBio®). AR2G tips were first rehydrated in ddH2O for 10 minutes in the loading tray. Upon initiation of the OCTET protocol, tips were then transferred to a secondary hydration solution of ddH2O for 60 seconds to make sure there are no aberrant readings. After rehydration, the tips were activated in freshly mixed 20 mM 1-Ethyl-3-[3-dimethylaminopropyl]carbodiimide hydrochloride (EDC), 10 mM sulfo-N-hydroxysulfosuccinimide (s-NHS) for 300 seconds. Antibodies being bound to the AR2G tips were diluted to 20 µg/ml in 10 mM Sodium Acetate, pH 5.0. After the AR2G tips were activated, they were placed in the antibody solution for 600 seconds. The tips were then quenched in 1M Ethanolamine, pH 8.5 for 300 seconds. After quenching, the tips were moved into Kinetics Buffer for 120 seconds to get a baseline reading. Soluble C5b-9 (CompTech, A127) was diluted to 30 µg/ml in Kinetics Buffer (KB). After baseline, the antibody bound tips were placed in the soluble C5b-9 solution for 300 seconds to measure association. The tips were finally returned to the KB solution where baseline was measured and a disassociation step was measured for 600 seconds. The level of deflection from baseline at 300 seconds of association was used as an indicator of binding affinity. All solutions used were in 200 µl volumes per well in a 96 well flat bottom black plate (Greiner Bio-One, 655209). The OCTET protocol was run at 1000 rpm and 30° C.

Figure 11A:
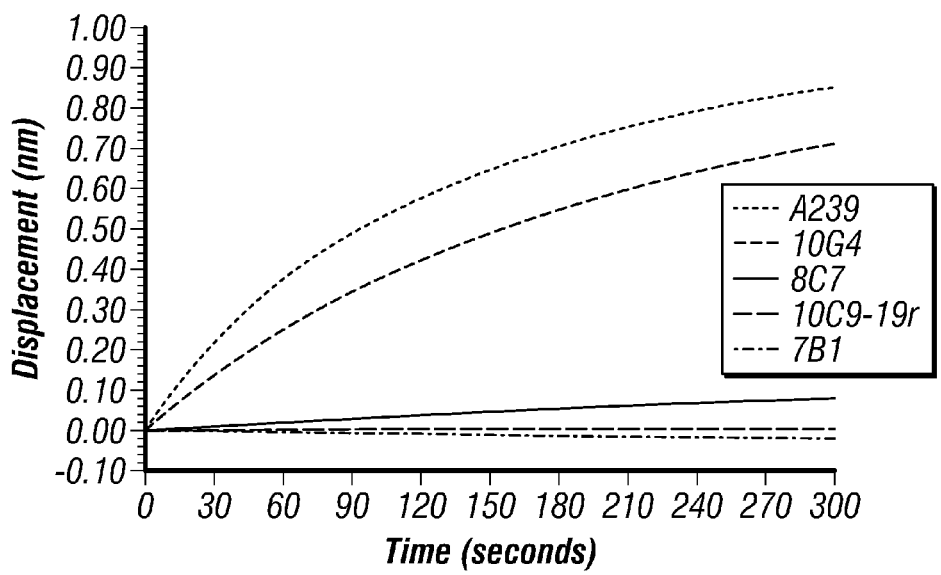
FIGS. 11a and 11b show the ability of the monoclonal antibodies to bind soluble C5b-9 using Bio-Layer Interferometry (BLI) technology.
Figure 11B:
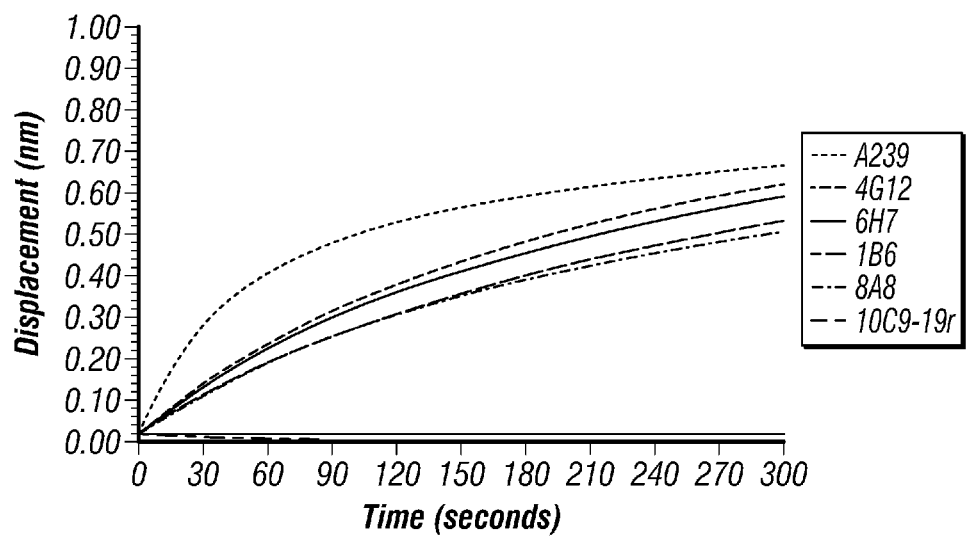

Results are shown in FIGS. 11A and 11B. The Quidel A239 antibody (labelled A239 in FIGS. 11A and 11B), serves as a positive control as it binds to C5b-9 (part of the MAC). From the results, as expected, no/very little binding was observed with the 10C9-19r antibody. This is consistent with the hypothesis that 10C9 (and its progeny/subclones) do not bind to soluble C5b-9.

Example 9

C5a Generation Assay 96-well EIA plates (Costar #3590) were coated with 2 µg/ml Human IgM in coating buffer pH 9.5. (BD-biosciences 51-2713KC) overnight at 4° C. Plates were washed using wash buffer (BD-biosciences 51-9003739). Serum diluted to 10% in GVB (BD-biosciences 51-2713KC) in the presence or absence of purified IgGs (anti-C5 antibodies) and incubated for 20 minutes at 4° C. After the incubation period 100 µl of the serum/antibody mixture is added to the washed IgM coated plates and incubated for 1 hr at 37° C. After the incubation supernatant was collected. Levels of C5a in the supernatant were then determined using Micro-Vue C5a EIA Kit (Quidel, cat#A021).

Figure 6A:
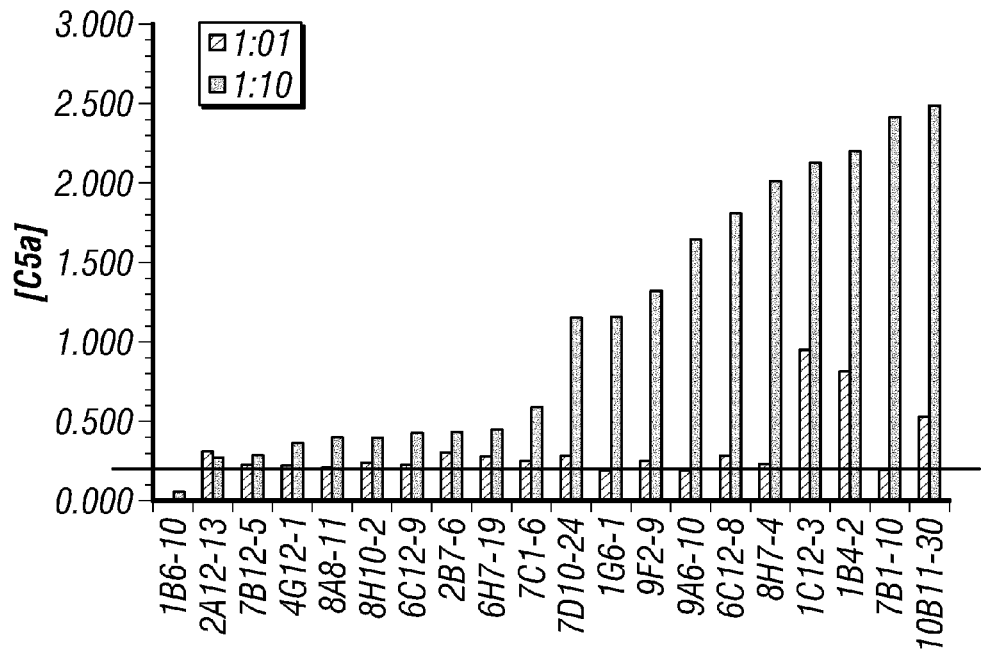
FIGS. 6A, 6B and 6C show the generation of C5a inhibition by examining single point determinations or by titration of the antibody.
Figure 6B:
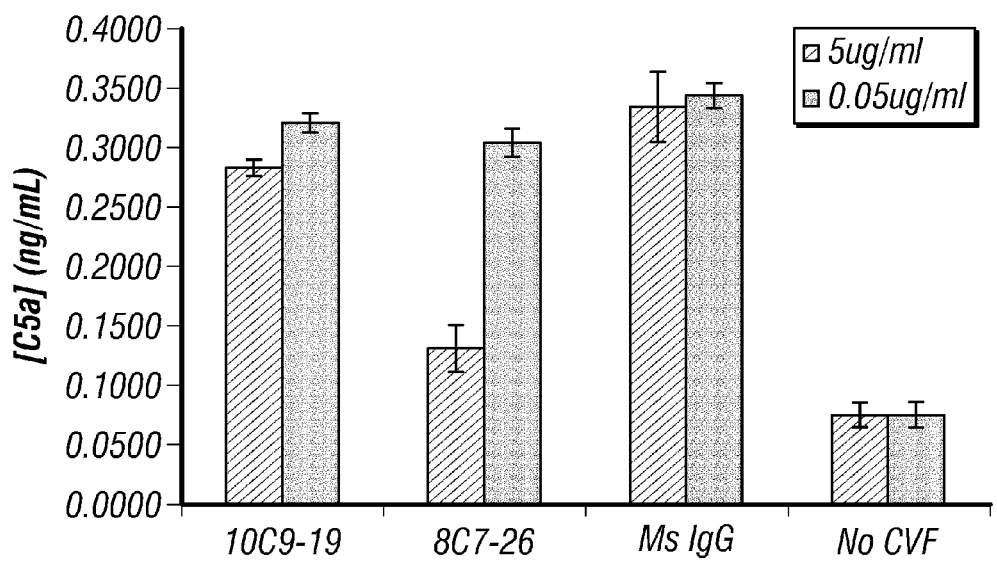
Figure 6C:
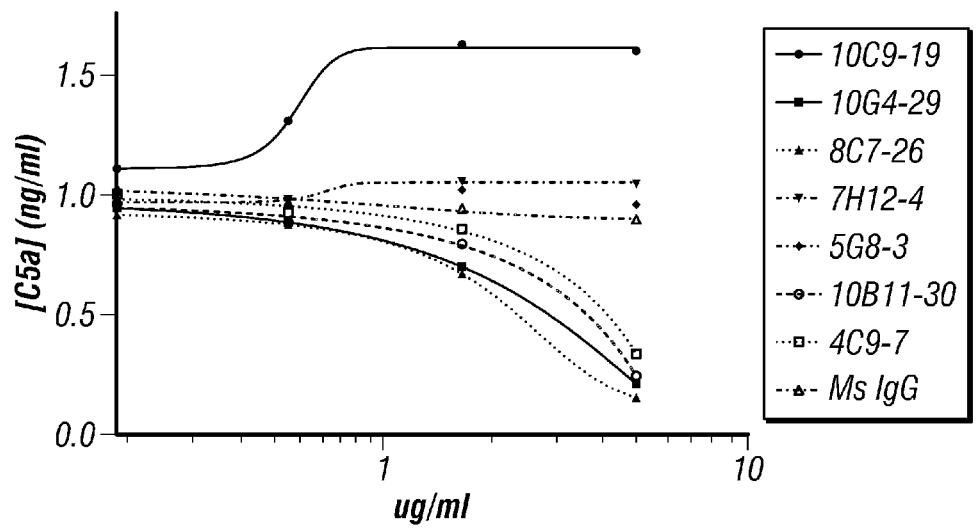

FIGS. 6A, 6B, and 6C show the results of the assay. FIG. 6A shows levels of C5a in the supernatant for selected anti-C5 antibodies that were screened. The black horizontal line depicts background levels. As seen from the graph, some antibodies were better than others in blocking C5a formation. FIG. 6B compares 10C9-19 antibody in C5a formation. As seen in the graph, Ms IgG condition served as a positive control and the "No CVF" (no Cobra Venom Factor) control served as a no protease negative control. At the 5 µg/ml concentration, another anti-C5 antibody, 8C7-26 inhibited C5a formation, but did not inhibit C5a formation at the 0.05 ug/ml concentration. However, 10C9-19 does not inhibit C5a formation at either the 5 µg/ml nor at the 0.05 ug/ml concentration.

Example 10

Statistical Analysis

The following describes how percent inhibition and other statistical analysis was performed in the experiments included in this Example section.

Hemolytic Assay: % inhibition=1−((*T−N*)/(*P−N*))*100

T is test OD (level of hemoglobin released during the assay)

N=negative control OD (hemoglobin release within the assay under conditions in which complement activity has been blocked by addition of EDTA to 10 mM)

P=positive control OD (hemoglobin release when erythrocytes are incubated in the presence of serum in the absence of an inhibitor, this represents 100% activity).

Z-Factor: Z-factor=1−((3*(*Dp−Dn*))/(abs(*Mp−Mn*)))

where Dp is standard deviation of positive control, Dn is standard deviation of negative control, Mp is mean of positive control, and Mn is mean of negative control.

IC90: $Y=Ymin+(Ymax-Ymin)/(1+10^{(ECx-Curve)})$ fit (Graphpad Prism)

where ECx is log IC90−(1/m)*log(90/(100−90)).

Example 11

Immunization of C5 Deficient Mice

Immunization of C5 deficient mice allowed the generation of hybridoma cell culture supernatants that are capable of inhibiting complement mediated red blood cell lysis as determined by the CH50 hemolytic assay. The response by the selected hybridomas was much greater than that seen using conventional commercially available antibodies indicated by the black line in FIG. 3.

Figure 4A:
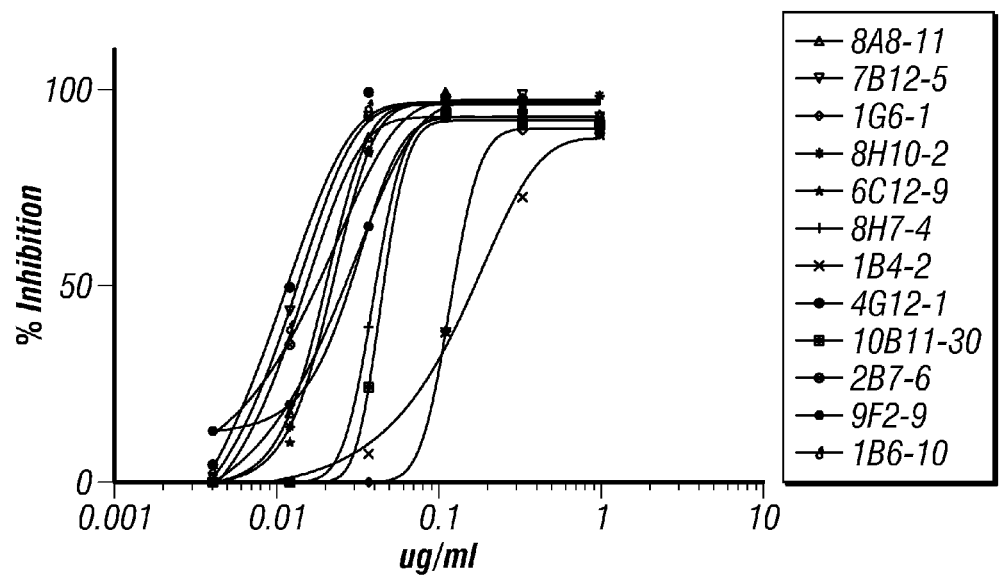
FIGS. 4A and 4B show percent inhibition of MAC by anti-C5 antibody sub-clones.
Figure 4B:
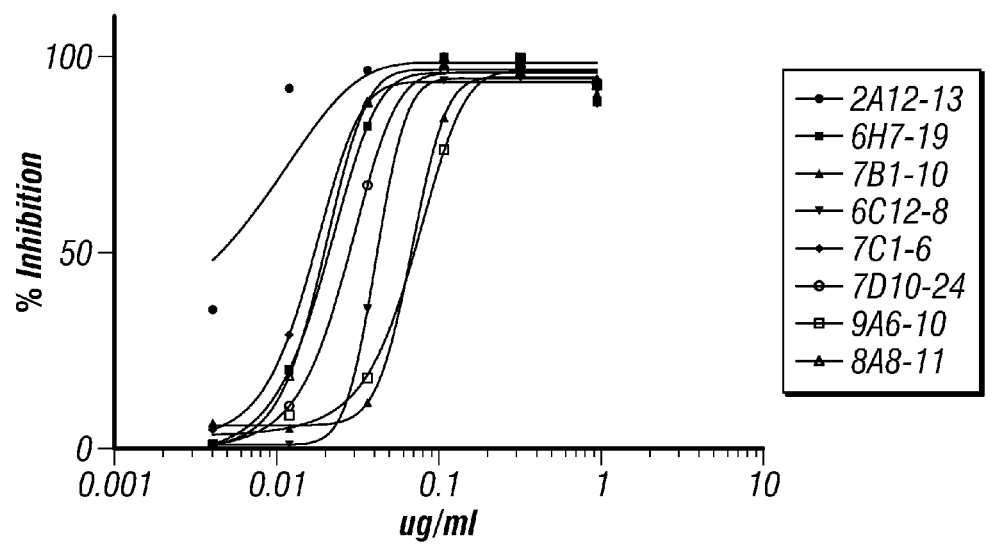

Expansion and cloning of the primary of the hybridomas with sequential purification of IgG allow the analysis of function and efficacy in blocking complement mediated cell lysis by titrating the concentration of the IgG. A more thorough understanding of the relative efficacy of a give monoclonal to inhibit complement mediated cell lysis is obtained, as shown in FIGS. 4A and 4B.

The functional activity of anti C5 monoclonal antibodies can be characterized based on efficacy for inhibiting a select complement pathways. Inhibitory antibodies were selected based on the particular pathway in which they inhibit, shown in FIGS. 5A, 5B, and 5C.

Blocking cell lysis can occur by either preventing the assembly of the membrane attack complex or by the blocking of the conversion of C5 to C5b by the C5 convertase. Further characterization allows one to examine the mechanism of inhibition, i.e. if the inhibitory reagent disrupts the proteolytic cleavage of C5 leading to generation of C5b and assembly of C5b-9 complex or only block assemblage of the C5b-9 complex without blocking generation of C5a. In the latter case identification of inhibitors blocking convertase activity was identified by examining the generation of C5a which is an obligatory by product in the production of C5b. This was done by examining single point determinations or by titration of the antibody, shown in FIGS. 6A, 6B and 6B.

Specificity of a monoclonal antibody for C5 was identified by examining its interaction dose dependent interaction with C5 directly coated on to an ELISA plates, shown in FIG. 7.

Figures 8, 9:
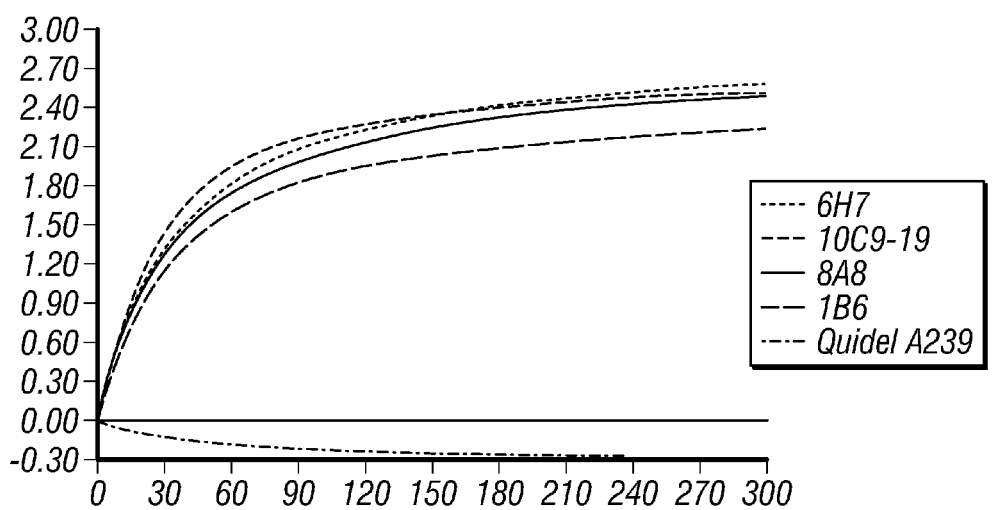
FIG. 8 shows binding affinities of anti-C5 monoclonal antibodies to C5.
FIG. 9 shows the binding of the monoclonal antibodies to C5 protein in solution using Bio-Layer Interferometry (BLI).

Further characterization can occur by studying the affinity of monoclonal antibodies using Bio-layer interferometry (BLI) allowing identification of KD values and relative specificity of the monoclonal antibodies, shown in FIG. 8. Additional characterization was obtained by studying the binding of the monoclonal antibodies to C5 protein in solution, shown in FIG. 9.

Example 12

Selection of C5 Antibodies

One preferred embodiment is the selection for antibodies that do not recognize C5 once it is incorporated into the membrane attack complex. Monoclonal antibodies were examined according to the ability to recognize C5 with in the C5b-9 complex when deposited into the bottom of ELISA plates after complement activation with IgM, shown in FIG. 10.

Further cross reactivity with C5 within C5b-9 was identified by examining the ability of the monoclonal to bind soluble C5b-9 using Bio-layer interferometry (BLI) and determining the level of deflection, shown in FIG. 11.

Example 13

Generation of Humanized Antibodies

A lead antibody was selected and humanized. The humanization method of string content optimization (Lazar et al, US7657380B2, issued Feb. 2, 2010; US7930107B2, issued Apr. 19, 2011; US20060008883A1, filed Dec. 3, 2004; US20080167449A1, filed Oct. 31, 2007; US20110236969A1, filed Mar. 21, 2011; US20100190247A1, filed Mar. 12, 2012, all incorporated entirely by reference) was applied to the murine 10C9 antibody. Selected humanized sequences are listed in SEQ ID NOs:1-12 and Table 2.

Figure 12A:
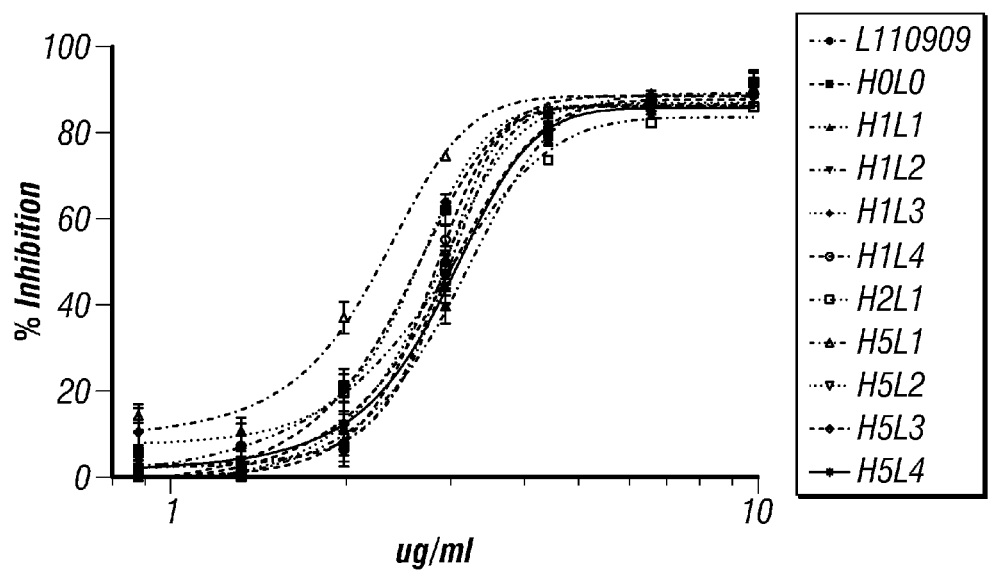
FIGS. 12A, 12B and 12C show inhibition of MAC for full-length antibodies with humanized heavy and light chains of 10C9.
Figure 12B:
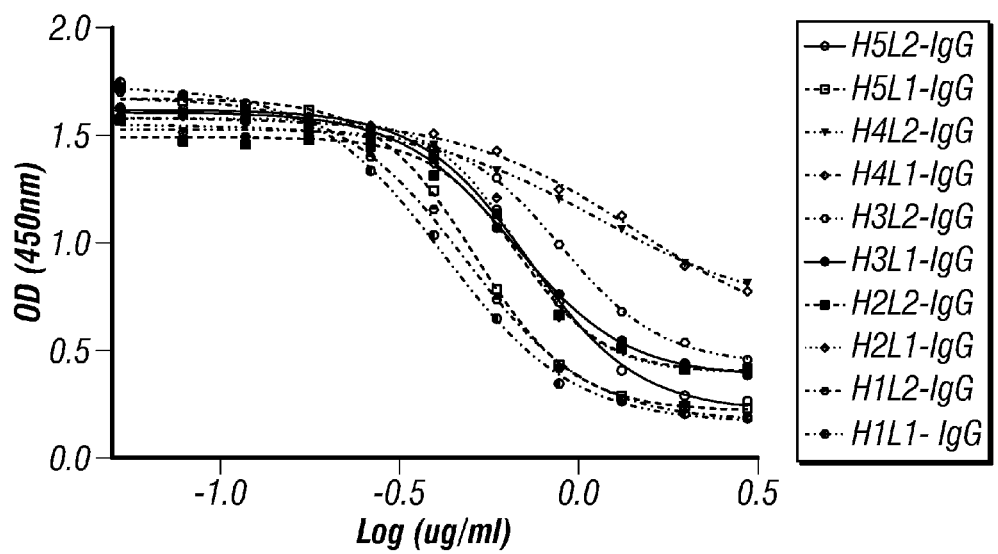
Figure 12C:
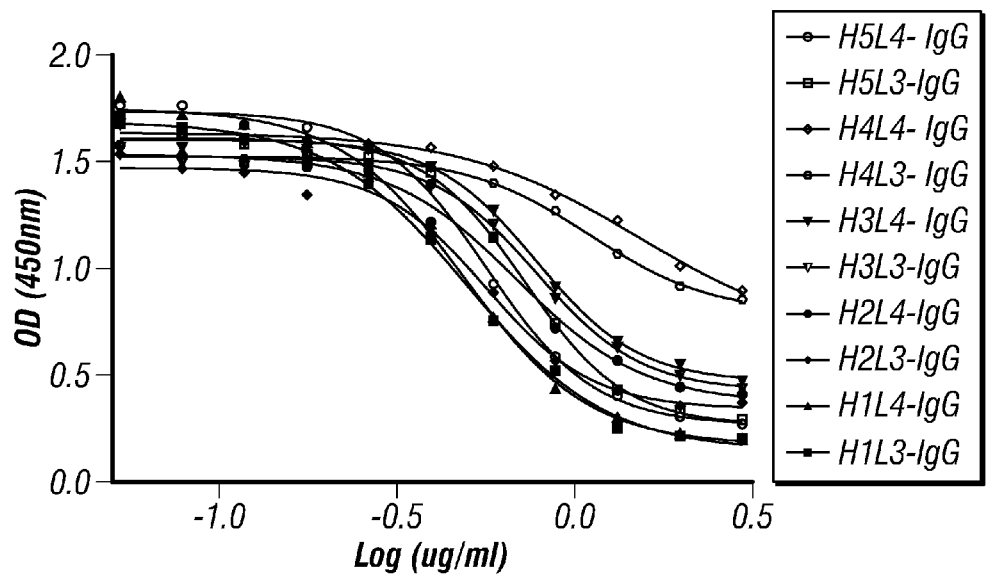
Figure 13A:
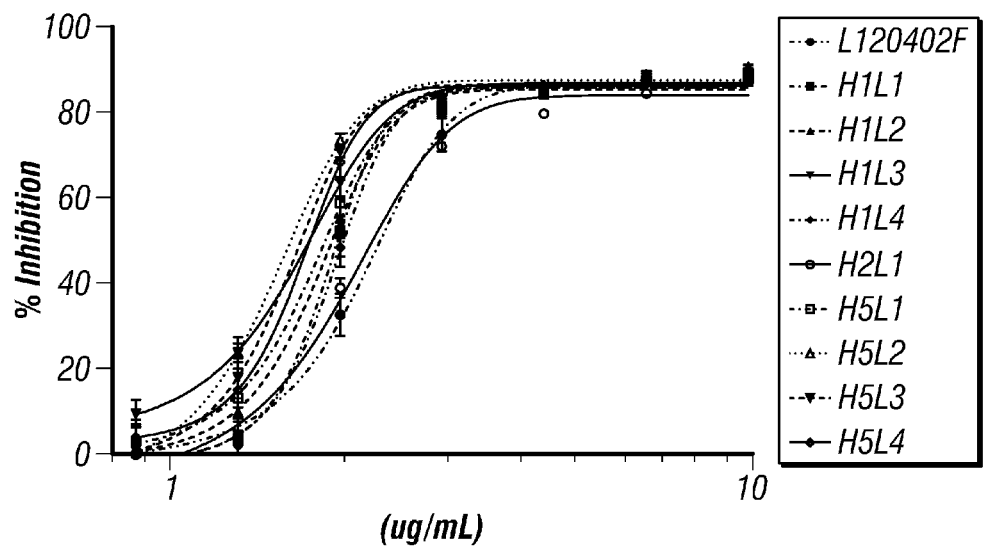
FIGS. 13A, 13B, and 13C show activity of Fab fragments with humanized heavy and light chains of 10C9.
Figure 13B:
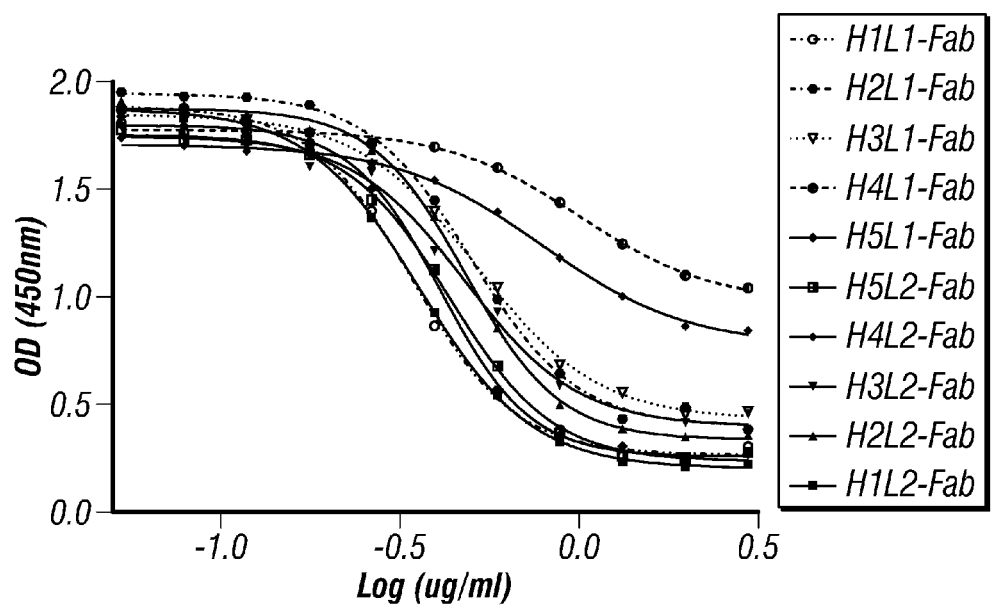
Figure 13C:
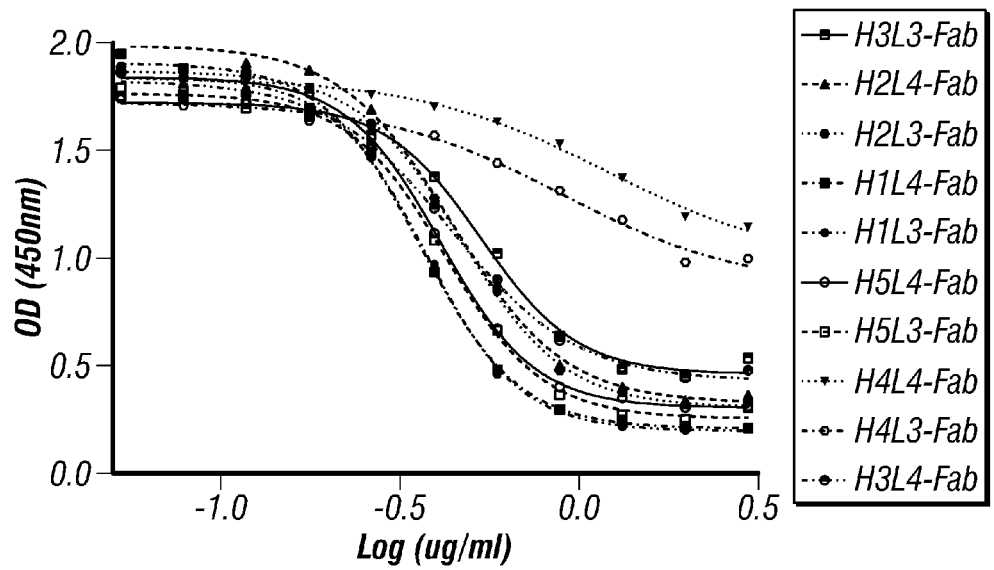

Using standard techniques, the IgGs were produced. Percent inhibition is shown in FIGS. 12A, 12B and 12C for full-length antibodies using the ELISA assay that was described in Example 6 above. Additionally, Fab fragments were produced using standard techniques and their activity similar to that of the parent molecule, using the ELISA assay that was described in Example 6. Graphical representation of the results is shown in FIGS. 13A, 13B, and 13C.

Example 14

Figure 14A:
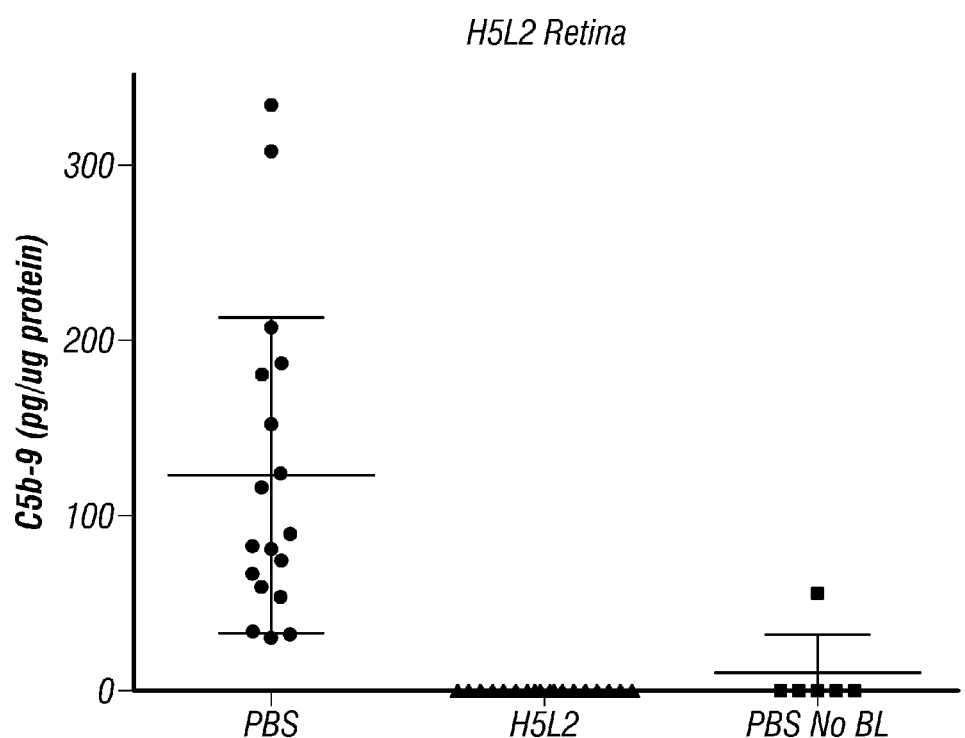
FIGS. 14 A and 14B shows the H5L2 (humanized 10C9) antibody is effective in a non-human primate light injury model in blocking complement deposition in retina (FIG. 14A) and choroid (FIG. 14B) relative to control.
Figure 14B:
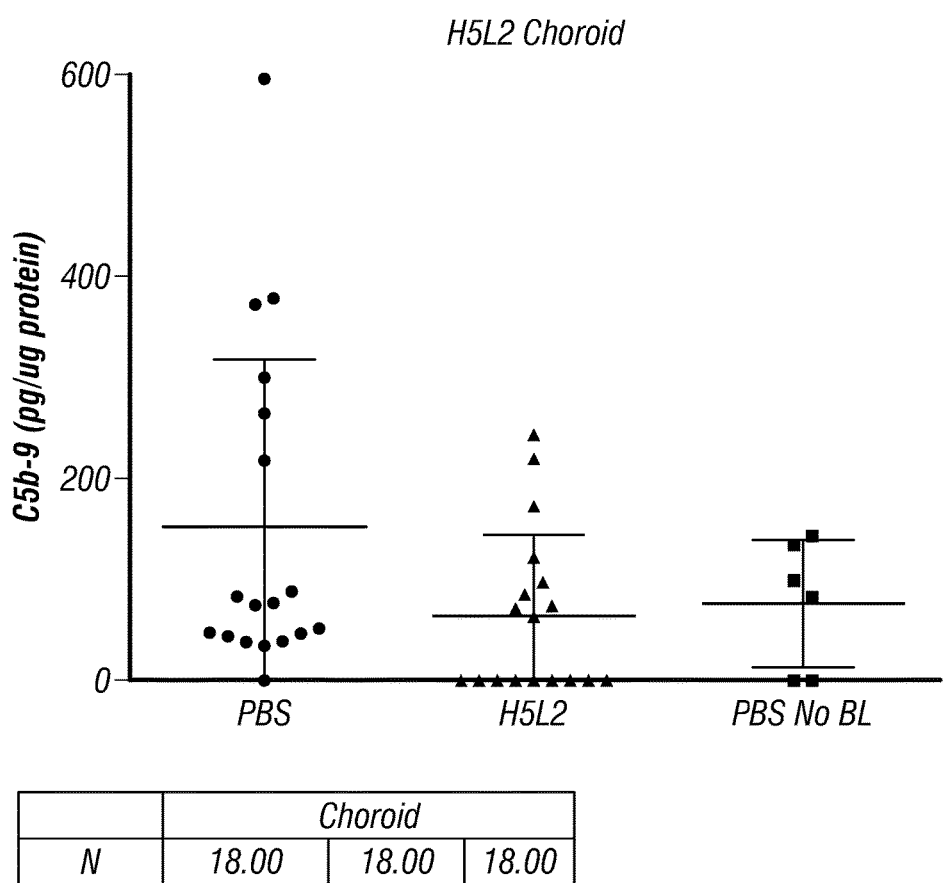

Use of C5 Antibody for Prevention of C5b-9 Deposition in Retinal and Choroidal Tissues Additionally, the therapeutic potential of a compound by intravitreal delivery in blocking C5b-9 formation in retinal and choroidal tissues can be assessed by use of standard models leading to complement activation in tissues of interest as provided in, AL-78898A Inhibits Complement Deposition in a Primate Light Damage Model, ARVO Ab A387 2012. Humanized H5L2 (SEQ ID NO:10 and SEQ ID NO: 2, respectively) antibody was humanized from the mouse monoclonal antibody subclone 10C9. H5L2 was tested in a non-human primate light injury model. Intravitreal dosing of the H5L2 antibody provided efficacy in blocking complement deposition in the retina that was comparable to the negative control (PBS, no light injury, labeled "PBS No BL"). Positive control of PBS with light injury (labeled "PBS") was also used. Graphical representation of the results is shown in FIGS. 14A (retina) and 14B (choroid). These data indicate that local delivery of the H5L2 antibody is efficacious in an in vivo model relevant to the treatment of macular degeneration and other ocular indications.

We claim:

1. An anti-C5 antibody, wherein the antibody binds to C5 and inhibits complement dependent hemolysis, but does not block C5a formation, wherein the antibody comprises a first amino acid sequence and a second amino acid sequence, further wherein:
   (a) the first sequence comprising;
      (i) a CDR1 selected from the group consisting of SEQ ID NOs:13, 19, 25, 31, 37 and 43;
      (ii) a CDR2 selected from the group consisting of amino acids sequence GTS (SEQ ID NOS: 14 and 20), SGS (SEQ ID NO: 26), RTS (SEQ ID NO: 32), YTS (SEQ ID NO: 38), and WAS (SEQ ID NO: 44); and
      (iii) a CDR3 selected from the group consisting of SEQ ID NOs:15, 21, 27, 33, 39 and 45; and
   (b) the second sequence comprising
      (i) a CDR1 selected from the group consisting of SEQ ID NOs:16, 22, 28, 34, 40 and 46;
      (ii) a CDR2 selected from the group consisting of SEQ ID NOs:17, 23, 29, 35, 41 and 47; and
      (iii) a CDR3 selected from the group consisting of SEQ ID NOs:18, 24, 30, 36, 42 and 48.

2. The antibody of claim 1, wherein the antibody blocks C5 binding to human Complement Component 6 and/or 7.

3. The antibody of claim 1, wherein the antibody inhibits formation of membrane attack complex (MAC).

4. The antibody of claim 1, further comprising a heavy chain and a light chain wherein:
   the light chain comprises an amino acid sequence identical to a sequence selected from the group consisting of SEQ ID NO:1, 3, 5, 7, 9, and 11; and
   the heavy chain comprises an amino acid sequence identical to a sequence selected from the group consisting of SEQ ID NO:2, 4, 6, 8, 10, and 12.

5. The antibody of claim 1, wherein the antibody comprises a light chain and a heavy chain variable domain selected from the light chain and heavy chain variable sequences: SEQ ID NO:1/SEQ ID NO:2; SEQ ID NO:3/SEQ ID NO:4; SEQ ID NO:5/SEQ ID NO:6; SEQ ID NO:7/SEQ ID NO:8; SEQ ID NO:9/SEQ ID NO:10; SEQ ID NO:11/SEQ ID NO:12; and SEQ ID NO:3/SEQ ID NO:10.

6. The antibody of claim 1, wherein the antibody is a monoclonal antibody, a polyclonal antibody, a recombinant antibody, a humanized antibody, a chimeric antibody, a multispecific antibody, or an antibody fragment thereof.

7. The antibody of claim 6, wherein the antibody is an antibody fragment and the antibody fragment is a Fab fragment, a Fab' fragment, a F(ab')2 fragment, a Fv fragment, a diabody, or a single chain antibody molecule.

8. The antibody of claim 6, wherein said antibody is of the IgG1-, IgG2-IgG3- or IgG4-type.

9. The antibody of claim 8, wherein the antibody is of an IgG1-type.

10. The antibody of claim 1, wherein the antibody is coupled to a labelling group.

11. The antibody of claim 10, wherein the labelling group is an optical label, radioisotope, radionuclide, an enzymatic group, and a biotinyl group.

12. A method for treating or reducing the occurrence of an indication associated with complement activation in a patient in need thereof;
   comprising administering to said patient an effective amount of the antibody of claim 1;
   and thereby treating or reducing the occurrence of the indication.

13. The method of claim 12, wherein the condition is an ocular condition.

14. The method of claim 13, wherein the condition is age-related macular degeneration.

* * * * *

SEQUENCE LISTING

```
<160> NUMBER OF SEQ ID NOS: 53

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Asp Val Asn Thr Ala
                20                  25                  30

Val Ala Trp Tyr Gln Gln Lys Pro Asp Gln Ser Pro Lys Leu Leu Ile
            35                  40                  45

Tyr Trp Ala Ser Thr Arg His Thr Gly Val Pro Ala Arg Phe Thr Gly
        50                  55                  60

Ser Gly Ser Gly Thr Asp Tyr Thr Leu Thr Ile Ser Ser Leu Gln Ala
65                  70                  75                  80

Glu Asp Val Ala Val Tyr Phe Cys Gln Gln His His Val Ser Pro Trp
                85                  90                  95

Thr Phe Gly Gly Gly Thr Lys Val Glu Ile Lys
                100                 105

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Glu
            20                  25                  30

Tyr Met Asn Trp Val Arg Gln Ala Pro Gly Gln Ser Leu Glu Trp Met
        35                  40                  45

Gly Tyr Ile Asn Pro Asn Gly Gly Ala Asp Tyr Asn Gln Lys Phe
    50                  55                  60

Gln Gly Arg Val Thr Met Thr Val Asp Gln Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Leu Gly Tyr Ser Asn Pro Tyr Phe Asp Phe Trp Gly Gln Gly
            100                 105                 110

Thr Leu Val Thr Val Ser Ser
            115

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Val Asn Thr Ala
            20                  25                  30

Val Ala Trp Tyr Gln Gln Lys Pro Asp Gln Ser Pro Lys Leu Leu Ile
        35                  40                  45

Tyr Trp Ala Ser Thr Arg His Thr Gly Val Pro Ala Arg Phe Thr Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln His His Val Ser Pro Trp
                85                  90                  95

Thr Phe Gly Gly Gly Thr Lys Val Glu Ile Lys
            100                 105

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Glu
            20                  25                  30

Tyr Met Asn Trp Val Arg Gln Ala Pro Gly Lys Ser Leu Glu Trp Val
        35                  40                  45
```

```
Gly Tyr Ile Asn Pro Asn Asn Gly Gly Ala Asp Tyr Asn Gln Lys Phe
        50                  55                  60

Gln Gly Arg Val Thr Ile Thr Val Asp Gln Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Leu Gly Tyr Ser Asn Pro Tyr Phe Asp Phe Trp Gly Gln Gly
                100                 105                 110

Thr Leu Val Thr Val Ser Ser
            115

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Leu Thr Gln Ser Pro Ser Phe Leu Ser Ala Ser Val Gly
 1               5                  10                  15

Asp Arg Val Thr Ile Thr Cys Gln Ala Ser Gln Asp Val Asn Thr Ala
                 20                  25                  30

Val Ala Trp Tyr Leu Gln Lys Pro Gly Lys Ser Pro Lys Leu Leu Ile
             35                  40                  45

Tyr Trp Ala Ser Thr Arg His Thr Gly Val Pro Ala Arg Phe Thr Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln His His Val Ser Pro Trp
                 85                  90                  95

Thr Phe Gly Gly Gly Thr Lys Val Glu Ile Lys
                100                 105

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Glu
                 20                  25                  30

Tyr Met Asn Trp Val Arg Gln Ala Pro Gly Gln Ser Leu Glu Trp Met
             35                  40                  45

Gly Tyr Ile Asn Pro Asn Asn Gly Gly Ala Asp Tyr Asn Pro Ser Leu
        50                  55                  60

Lys Ser Arg Val Thr Ile Ser Val Asp Gln Ser Ile Ser Thr Ala Tyr
 65                  70                  75                  80

Met Glu Leu Ser Arg Leu Arg Ser Asp Asp Thr Ala Val Tyr Phe Cys
                 85                  90                  95

Ala Arg Leu Gly Tyr Ser Asn Pro Tyr Phe Asp Phe Trp Gly Gln Gly
                100                 105                 110
```

```
Thr Leu Val Thr Val Ser Ser
        115

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Val Asn Thr Ala
            20                  25                  30

Val Ala Trp Tyr Gln Gln Lys Pro Gly Lys Ser Pro Lys Leu Leu Ile
        35                  40                  45

Tyr Trp Ala Ser Thr Arg His Thr Gly Val Pro Ala Arg Phe Thr Gly
50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln His His Val Ser Pro Trp
                85                  90                  95

Thr Phe Gly Gly Gly Thr Lys Val Glu Ile Lys
            100                 105

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Leu Val Lys Pro Gly Gly
1               5                   10                  15

Ser Leu Arg Leu Ser Cys Ala Ala Ser Gly Tyr Thr Phe Thr Asp Glu
            20                  25                  30

Tyr Met Asn Trp Val His Gln Ala Pro Gly Lys Ser Leu Glu Trp Val
        35                  40                  45

Gly Tyr Ile Asn Pro Asn Asn Gly Ala Asp Tyr Asn Pro Ser Leu
50                  55                  60

Lys Ser Arg Val Thr Ile Ser Val Asp Gln Ser Lys Ser Ile Ala Tyr
65                  70                  75                  80

Leu Gln Met Asn Ser Leu Lys Thr Glu Asp Thr Ala Val Tyr Phe Cys
                85                  90                  95

Ala Arg Leu Gly Tyr Ser Asn Pro Tyr Phe Asp Phe Trp Gly Gln Gly
            100                 105                 110

Thr Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 9

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Ala Arg Phe Thr Gly
50                  55                  60

Ser Gly Ser Gly Thr Asp Tyr Thr Leu Thr Ile Ser Ser Leu Gln Ser
65                  70                  75                  80

Glu Asp Phe Ala Val Tyr Phe Cys Gln Gln His His Val Ser Pro Trp
                85                  90                  95

Thr Phe Gly Gly Gly Thr Lys Val Glu Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Lys Gln Ser Gly Ala Glu Val Lys Lys Pro Gly Ala
1               5                   10                  15

Ser Val Lys Val Ser Cys Lys Ala Ser Gly Tyr Thr Phe Thr Asp Glu
            20                  25                  30

Tyr Met Asn Trp Val Arg Gln Ala Pro Gly Lys Ser Leu Glu Trp Met
        35                  40                  45

Gly Tyr Ile Asn Pro Asn Asn Gly Ala Asp Tyr Asn Gln Lys Phe
50                  55                  60

Gln Gly Arg Val Thr Met Thr Val Asp Gln Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Leu Gly Tyr Ser Asn Pro Tyr Phe Asp Phe Trp Gly Gln Gly
            100                 105                 110

Thr Leu Val Thr Val Ser Ser
        115

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Ser Phe Leu Ser Ala Ser Val Gly
1               5                   10                  15

Asp Arg Val Thr Ile Thr Cys Gln Ala Ser Gln Asp Val Asn Thr Ala
            20                  25                  30

Val Ala Trp Tyr Gln Gln Lys Pro Gly Lys Ser Pro Lys Leu Leu Ile
        35                  40                  45

Tyr Trp Ala Ser Thr Arg His Thr Gly Val Pro Ala Arg Phe Thr Gly
```

```
                    50                  55                  60
Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln His His Val Ser Pro Trp
                     85                  90                  95

Thr Phe Gly Gly Gly Thr Lys Val Glu Ile Lys
                100                 105
```

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asp Glu
                20                  25                  30

Tyr Met Asn Trp Val Arg Gln Ala Pro Gly Lys Ser Leu Glu Trp Met
             35                  40                  45

Gly Tyr Ile Asn Pro Asn Asn Gly Ala Asp Tyr Asn Gln Lys Phe
         50                  55                  60

Gln Gly Arg Val Thr Met Thr Val Asn Gln Ser Ile Ser Thr Ala Tyr
 65                  70                  75                  80

Met Glu Leu Ser Arg Leu Arg Ser Asp Asp Thr Ala Val Tyr Phe Cys
                 85                  90                  95

Ala Arg Leu Gly Tyr Ser Asn Pro Tyr Phe Asp Phe Trp Gly Gln Gly
                100                 105                 110

Thr Leu Val Thr Val Ser Ser
        115
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Ser Ser Ile Ser Ser Ser Asn
 1               5
```

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Gly Thr Ser
 1
```

<210> SEQ ID NO 15
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 15

Gln Gln Trp Ser Ser Tyr Pro Phe Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Tyr Thr Phe Thr Asp Tyr Glu
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Asp Pro Glu Thr Gly Gly Ala
1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Arg Leu Gly Ser Ser Pro Trp Tyr Phe Asp Val
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ser Ile Ser Ser Ser Asn
1               5

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Thr Ser
1
```

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Trp Ser Thr Tyr Pro Phe Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Thr Phe Thr Asp Tyr Glu
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Asp Pro Glu Thr Gly Gly Thr
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Arg Leu Gly Ile Ser Pro Trp Tyr Phe Asp Val
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Ser Ile Ser Lys Tyr
1               5

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Ser Gly Ser
1

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln His Asn Glu Tyr Pro Tyr Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Arg Phe Thr Asp Tyr Asn
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Ser Pro Asn Asn Gly Gly Thr
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Arg Glu Ala Trp Tyr Gly Gly Tyr Tyr Lys Trp Tyr Phe Asp
1               5                   10                  15

Val

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Ile Ser Ser Asn Tyr
1               5

<210> SEQ ID NO 32
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Thr Ser
1

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Gly Ser Gly Ile Phe Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Tyr Thr Phe Thr Thr Tyr Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Asn Thr Tyr Ser Gly Val Pro
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Arg Arg Asp Phe Tyr Gly Asn Tyr Gly Asp Tyr
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Gln Asp Ile Ser Ser Tyr
1               5

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Thr Ser
1

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Gly Asn Val Phe Pro Trp Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Thr Phe Thr Asp Ser Tyr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Leu Pro Asn Asn Gly Gly Ile
1               5

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Arg Ser Gly Gly Leu Val Gly Gly Tyr Phe Asp Tyr
1               5                   10

<210> SEQ ID NO 43
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 43

Gln Asp Val Asn Thr Ala
1               5

<210> SEQ ID NO 44
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ala Ser
1

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln His His Val Ser Pro Trp Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Thr Phe Thr Asp Glu Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Asn Pro Asn Asn Gly Gly Ala
1               5

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Leu Gly Tyr Ser Asn Pro Tyr Phe Asp Phe
1               5                   10
```

-continued

```
<210> SEQ ID NO 49
<211> LENGTH: 276
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (125)..(125)
<223> OTHER INFORMATION: Inosine

<400> SEQUENCE: 49
gggaattcat grasttskgg ytmarctkgr tttgggaatt catgraatgs asctgggtyw      60
tyctcttact agtcgacatg aagwtgtggb traactggrt actagtcgac atggratgga    120
sckknrtctt tmtctactag tcgacatgaa cttygggyts agmttgrttt actagtcgac    180
atgtacttgg gactgagctg tgtatactag tcgacatgag agtgctgatt cttttgtgac   240
tagtcgacat ggattttggg ctgattttt ttattg                                  276

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: Inosine

<400> SEQUENCE: 50
cccaagcttc cagggrccar kggataracn grtgg                                   35

<210> SEQ ID NO 51
<211> LENGTH: 328
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(48)
<223> OTHER INFORMATION: Inosine
<220> FEATURE:
<221> NAME/KEY: modified_base
<222> LOCATION: (54)..(54)
<223> OTHER INFORMATION: Inosine
<220> FEATURE:
<221> NAME/KEY: modified_base
<222> LOCATION: (60)..(60)
<223> OTHER INFORMATION: Inosine
<220> FEATURE:
<221> NAME/KEY: modified_base
<222> LOCATION: (90)..(90)
<223> OTHER INFORMATION: Inosine
<220> FEATURE:
<221> NAME/KEY: modified_base
<222> LOCATION: (102)..(102)
<223> OTHER INFORMATION: Inosine

<400> SEQUENCE: 51
gggaattcat gragwcacak wcycaggtct ttactagtcg acatgagnmm ktcnmttcan     60
ttcytgggac tagtcgacat gakgthcycn gctcagytyc tnrgactagt cgacatggtr   120
tccwcasctc agttccttga ctagtcgaca tgtatatatg tttgttgtct atttctacta   180
gtcgacatga agttgcctgt taggctgttg gtgctactag tcgacatgga tttwcargtg   240
```

```
cagattwtca gcttactagt cgacatggty ctyatvtcct tgctgttctg gactagtcga    300
catggtycty atvttrctgc tgctatgg                                      328

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cccaagctta ctggatggtg ggaagatgga                                    30

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 53

His His His His His His
1               5
```